US012637658B2

(12) United States Patent
Shiku et al.

(10) Patent No.: US 12,637,658 B2
(45) Date of Patent: May 26, 2026

(54) METHOD FOR GENE TRANSFER INTO GAMMA-DELTA TYPE T CELL

(71) Applicant: Mie University, Tsu (JP)

(72) Inventors: Hiroshi Shiku, Tsu (JP); Yoshihiro Miyahara, Tsu (JP); Satoshi Okumura, Tsu (JP); Takuma Kato, Tsu (JP); Tae Hayashi, Tsu (JP); Yoshimasa Tanaka, Nagasaki (JP)

(73) Assignee: MIE UNIVERSITY, Tsu (JP)

( * ) Notice: Subject to any disclaimer, the term of this patent is extended or adjusted under 35 U.S.C. 154(b) by 726 days.

(21) Appl. No.: 17/262,900

(22) PCT Filed: Jul. 31, 2019

(86) PCT No.: PCT/JP2019/029999

§ 371 (c)(1),
(2) Date: Jan. 25, 2021

(87) PCT Pub. No.: WO2020/027193

PCT Pub. Date: Feb. 6, 2020

(65) Prior Publication Data

US 2021/0161963 A1 Jun. 3, 2021

(30) Foreign Application Priority Data

Jul. 31, 2018 (JP) ................................ 2018-143207

(51) Int. Cl.

| | |
|---|---|
| ***C12N 5/0783*** | (2010.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61K 40/46*** | (2025.01) |
| ***C07K 14/725*** | (2006.01) |
| ***C12N 15/85*** | (2006.01) |

(52) U.S. Cl.

CPC ............ *C12N 5/0636* (2013.01); *A61K 40/11* (2025.01); *A61K 40/31* (2025.01); *A61K 40/32* (2025.01); *A61K 40/4211* (2025.01); *A61K 40/4258* (2025.01); *A61K 40/4268* (2025.01); *A61K 40/4269* (2025.01); *A61K 40/46* (2025.01); *C07K 14/7051* (2013.01); *C12N 15/85* (2013.01); *A61K 2239/31* (2023.05); *A61K 2239/38* (2023.05); *A61K 2239/48* (2023.05); *A61K 2239/50* (2023.05); *A61K 2239/57* (2023.05); *C12N 2500/42* (2013.01); *C12N 2510/00* (2013.01)

(58) Field of Classification Search

CPC ................ A61K 35/17; C07K 14/7051; C07K 14/5418; C07K 14/5443; C07K 2319/03; C12N 5/0636; C12N 15/85; C12N 2500/42; C12N 2510/00; C12N 15/86; C12N 2740/10043; C12N 2740/13043; A61P 31/00; A61P 35/00; A61P 35/02

See application file for complete search history.

(56) References Cited

U.S. PATENT DOCUMENTS

2017/0360811 A1* 12/2017 Tanaka .................... A61P 31/16
2018/0312808 A1* 11/2018 Hayday ................... A61P 31/12
2020/0172864 A1 6/2020 Chang et al.

FOREIGN PATENT DOCUMENTS

CN 102994448 A 3/2013
TW 201814042 A 4/2018
WO 2016/098904 A1 6/2016
WO 2017/072367 A1 5/2017

OTHER PUBLICATIONS

Inaguma et al. "Construction and molecular characterization of a T-cell receptor-like antibody and CAR-T cells specific for minor histocompatibility antigen HA-1H." Gene therapy 21.6 (2014): 575-584 (Year: 2014).*

Doglio et al, "IL-2 and IL-15 allow the generation of gamma-delta CAR-T cells with potent anti-leukaemia activity: A foundation for off-the-shelf cellular immunotherapy of haematological malignancies", Bone Marrow Transplantation, 2017, vol. 52, No. Suppl. 1, p. S166 (Year: 2017).*

Matsumoto et al. "Targeting cancer cells with a bisphosphonate prodrug." ChemMedChem 11.24 (2016): 2656-2663 (Year: 2016).*

Van Acker et al. "The role of the common gamma-chain family cytokines in γδ T cell-based anti-cancer immunotherapy." Cytokine & growth factor reviews 41 (2018): 54-64 (Year: 2018).*

International Search Report and Written Opinion, PCT/JP2019/029999, Japan Patent Office, Sep. 10, 2019.

Carding Sr and Egan PJ., "Gammadelta T cells: functional plasticity and heterogeneity." Nat Rev Immunol., 2(5): 336-345, 2002.

Deniger, D.C. et al., "Bispecific T-cells expressing polyclonal repertoire of endogenous γδ T-cell receptors and Introduced CD19-specific chimeric antigen receptor", Molecular Therapy, vol. 21, No. 3, pp. 638-647, Mar. 2013.

Doglio, M. et al., "IL-2 and IL-15 allow the generation of gamma-delta CAR-T cells with potent anti-leukaemia activity: A foundation for off-the-shelf cellular immunotherapy of haematological malignancies", Bone Marrow Transplantation, 2017, vol. 52, No. Suppl. 1, p. S166.

(Continued)

*Primary Examiner* — Fereydoun G Sajjadi
*Assistant Examiner* — Alexander W Nicol
(74) *Attorney, Agent, or Firm* — Gavrilovich, Dodd & Lindsey LLP

(57) ABSTRACT

The present invention provides a method for efficiently producing highly pure γδT cells introduced with foreign genes by culturing in the presence of IL-7 and IL-15 after stimulating the γδT cells with a bisphosphonic acid ester derivative. When a T cell receptor (TCR) or a chimeric antigen receptor (CAR) is introduced as a foreign gene, γδT cells in which TCR and CAR are functionally expressed can be obtained.

8 Claims, 18 Drawing Sheets

Specification includes a Sequence Listing.

(56) References Cited

OTHER PUBLICATIONS

Fisher et al., "Avoidance of on-target off-tumor activation using a co-stimulation-only chimeric antigen receptor", Molecular Therapy, May 2017, vol. 25, No. 5, pp. 1234-1247.
Groeper, C. et al., "Cancer/testis antigen expression and specific cytotoxic T lymphocyte responses in non small cell lung cancer", Int. J. Cancer, 2006, vol. 120, pp. 337-343.
Hiasa, Atsunori et al., "Dual specificity of αβ¥? TCR T cells: transformation of V¥9V?2 T cells with MAGE-A4143-153 specific α β type TCR genes", Proceedings of the Japanese Cancer Association, Aug. 25, 2007, vol. 66, p. 423.
Ishihara, Yuko et al., "A unique T-cell receptor amino acid sequence selected by human T-cell lymphotropic virus type 1 tax301-309-specific cytotoxic T cells in HLA-A24: 02-positive asymptomatic carriers and adult T-cell leukemia/lymphoma patients", Journal of Virology, Oct. 2017, vol. 91, Issue 19, e00974-17.
Kagemyama S, et al., "Adoptive transfer of MAGE-A4 T-Cell receptor gene-transduced lymphocytes in patients with recurrent esophageal cancer." Clin Cancer Res., 21(10): 2268-2277, 2015.
Maude SL, et al., "Chimeric antigen receptor T Cells for sustained remissions in leukemia." N Engl J Med., 371 (16):1507-1517, 2014.
Nicol AJ, et al. "Clinical evaluation of autologous gammadelta T cell-based immunotherapy for metastatic solid tumours." Br J Cancer., 05(6): 778-786, 2011.
Sagar, D. et al., "In vivo immunogenicity of Tax (11-19) epitope in HLA-A2/DTR transgenic mice: Implication for dendritic cell-based anti-HTLV-1 vaccine", Vaccine, 2014, vol. 32, pp. 3274-3284.
Shang, X. Y. et al., "Rational optimization of tumor epitopes using in silico analysis-assisted substitution of TCR contact residues", European Journal of Immunology, 2009, vol. 39, pp. 2248-2258.
Tanaka Y, et al., "Expansion of human γδ T cells for adoptive immunotherapy using a bisphosphonate prodrug." Cancer Sci., 109(3):587-599, Mar. 2018.
Wang, L. N. et al., "Efficient tumor regression by adoptively transferred CEA-specific CAR-T cells associated with symptoms of mild cytokine release syndrome", Oncoimmunology, 2016, vol. 5, No. 9, e1211218.
Fujisawa, Masaki, Office Action, Japan Patent Office, Application No. 2019-141009, Jul. 24, 2023.
Inagaki-Ohara et al., "Interleukin-15 preferentially promotes the growth of intestinal intraepithelial lymphocytes bearing γδ T cell receptor in mice", Eur. J. Immunol., Nov. 1997, 27:2885-2891.
Izumi et al., "Effect of common γ-chain family cytokines on the proliferation of γδ T cells", The 15th Annual Meeting of Japanese Association of Cancer Immunology, Jun. 30, 2011 to Jul. 1, 2011, 3 pgs.
Nada et al., "Enhancing adoptive cancer immunotherapy with Vγ2Vδ2 T cells through pulse zoledronate stimulation", Journal for Immuno Therapy of Cancer, Feb. 21, 2017, 5:9, 24 pgs.
Novak-Giese, Sabine, European Search Report, European Patent Office, Application No. 19845159.3, Apr. 4, 2022.
Novak-Giese, Sabine, European Search Report, European Patent Office, Application No. 19845159.3, Sep. 22, 2022.
Office Action, Application No. 201980048937.7, The State Intellectual Property Office of People's Republic of China, Jan. 25, 2024.
Office Action, Application No. 201980048937.7, The State Intellectual Property Office of People's Republic of China, Jun. 29, 2024.
Kobayashi et al., "Safety profile and anti-tumor effects of adoptive immunotherapy using gamma-delta T cells against advanced renal cell carcinoma: a pilot study", Cancer Immunol. Immunother., Apr. 2007, 56:469-476.
Kobayashi et al., "Phase I/II study of adoptive transfer of yöT cells in combination with zoledronic acid and IL-2 to patients with advanced renal cell carcinoma", Cancer Immunol. Immunother., Apr. 26, 2011, 60:1075-1084.

* cited by examiner (A)

γδT cells can be obtai ned in high purity by PTA stimulation (B)
A culture containing IL-7 and IL-15 is suitable for the proliferation of γδT cells Effective introduction of NY-ESO-1-specific TCR gene to γδT cells

NY-ESO-1$_{p157-165}$ peptide produces cytokine specifically.

γδT cells introduced with NY-ESO-1-specific TCR recognize tumor cells antigen-specifically and produce cytokine.

γδT cells introduced with p40Tax-specific TCR from HTLV-1 recognize tumor cells antigen-specifically and produce cytokine.

Effective introduction of CAR gene to γδT cells

**The γδT cells introduced with CAR which specifically recognizes MAGE-A4$_{p230\text{-}239}$ / HLA-A*02:01 complex recognizes tumor cells antigen-specifically.**

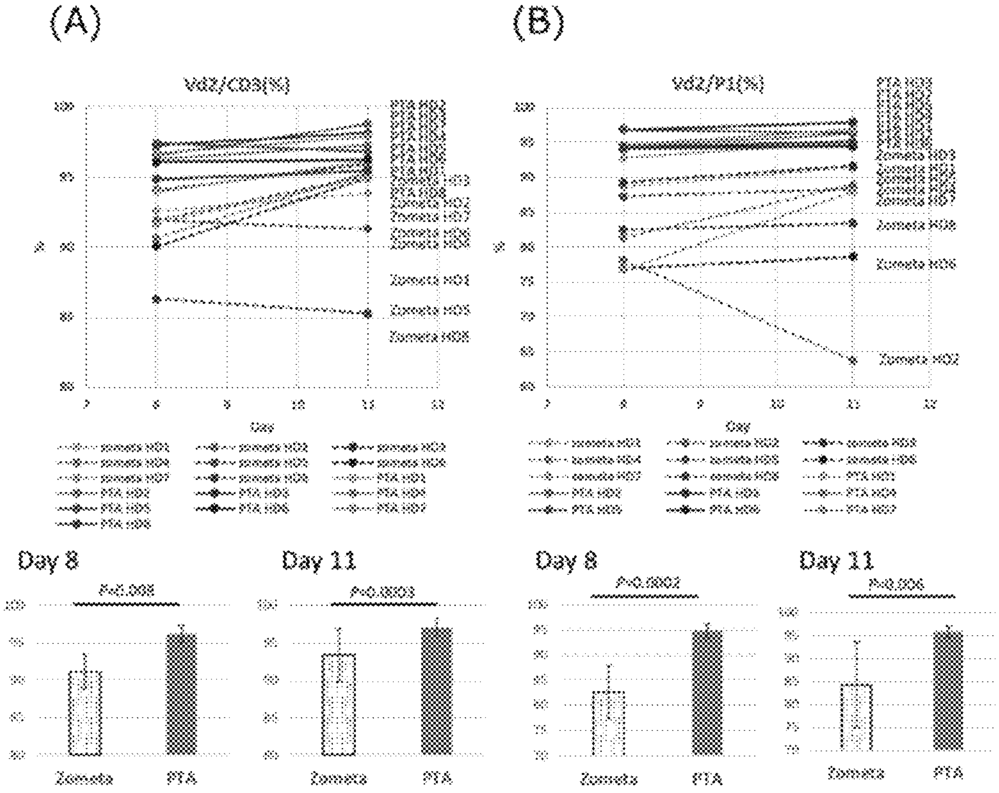
FIG. 14A-B

METHOD FOR GENE TRANSFER INTO GAMMA-DELTA TYPE T CELL

CROSS REFERENCE TO RELATED APPLICATIONS

This application is a U.S. National Phase Application filed under 35 U.S.C. § 371 and claims priority to International Application No. PCT/JP2019/029999, filed Jul. 31, 2019, which application claims priority to Japanese Application No. 2018-143207, filed Jul. 31, 2018, the disclosure of which are incorporated herein by reference.

TECHNICAL FIELD

The present invention relates to a method for efficiently producing high purity of γδT cells introduced with foreign genes.

BACKGROUND ART

In recent years, attentions have been paid to T cell infusion therapy as a treatment method for cancer, in which T cells newly imparted with cancer antigen specificity by transduction with a foreign gene encoding a T cell receptor (TCR) or a chimeric antigen receptor (CAR) are transferred into cancer patients. In fact, clinical trials have been conducted in which a TCR gene recognizing MAGE-A4, a cancer antigen, is introduced, and TCR gene modified T cells expressing the TCR is administered to patients with esophageal cancer (non-patent document 1). In addition, clinical trials have been conducted in which a CAR gene incorporating a single chain variable fragment (scFv) that bonds to CD19 is introduced into a ligand binding domain and CAR gene modified T cells expressing the CAR gene is administered to patients with acute lymphocytic leukemia which are intractable and difficult to be cured (non-patent document 2).

T cells having αβ-type TCR (GOT cells) are generally used as target cells for introducing foreign genes. The reason is as follows. That is, viral vector is mainly used for introducing foreign genes. However, it is normally necessary to proliferate and stimulate the target cells in the case. Besides, when the gene is introduced using the αβT cells as the target cells, the proliferation and stimulation of the target cells can be easily performed by using anti-CD3 antibody and anti-CD28 antibody.

T cells having γδ-type TCR (γδT cells) have been shown to injure virus-infected cells or cancer cells. An infusion therapy of γδT cells imparted with antigen specificity is expected to have a better effect than the case of using GOT cells. In fact, γδT-cell infusion therapy has been attempted (non-patent document 3). However, the analysis of the cytological characteristics such as the cell function of γδT cells is not sufficient. As a reason that can be given, the amount of γδT cells is as small as about 5% of the peripheral blood T cells (non-patent document 4). The number of cells required for the analysis of the cells is difficult to be secured. Unlike GOT cells, the γδT cells cannot be proliferated sufficiently by anti-CD3 antibody and anti-CD28 antibody. Accordingly, it has been attempted to proliferate γδT cells by using zoledronate which is a bisphosphonic acid derivative used as bone resorption inhibitor and interleukin-2 (IL-2) (non-patent documents 5 and 6). However, there is a problem of low purity of γδT cells obtained by expanded culture even when zoledronate and IL-2 are used.

A proliferation method of γδT cells with high purity by culturing monocyte obtained from human peripheral blood in the presence of tetrakispivaloyloxymethyl 2-(thiazole-2-ylamino) ethylidene-1,1-bisphosphonate, which is a bisphosphonic acid ester derivative, and further adding IL-2 to the culture has been reported (patent document 1 and non-patent document 7). On the other hand, in order to effectively carry out γδT cell infusion therapy, it is preferable to prepare highly pure γδT cells in a large amount, and introduce efficiently a foreign gene encoding TCR or CAR into the obtained γδT cells at the same time.

PRIOR ART DOCUMENTS

Patent Document

1. WO2016/098904

Non-Patent Documents

1. Kagemyama S, et al. Adoptive transfer of MAGE-A4 T-Cell receptor gene-transduced lymphocytes in patients with recurrent esophageal cancer. Clin Cancer Res. 2015 May 15; 21(10): 2268-2277.
2. Maude S L, et al. Chimeric antigen receptor T Cells for sustained remissions in leukemia. N Engl J Med. 2014 Oct. 16; 371(16):1507-1517.
3. Kobayashi H, et al. Safety profile and anti-tumor effects of adoptive immunotherapy using gamma-delta T cells against advanced renal cell carcinoma: a pilot study. Cancer Immunol Immunother. 2007 April; 56 (4):469-476.
4. Carding S R and Egan P J. Gammadelta T cells: functional plasticity and heterogeneity. Nat Rev Immunol. 2002 May; 2(5): 336-345.
5. Nicol A J, et al. Clinical evaluation of autologous gammadelta T cell-based immunotherapy for metastatic solid tumours. Br J Cancer. 2011 Sep. 6; 105(6): 778-786.
6. Kobayashi H, et al. Phase I/II study of adoptive transfer of γ8 T cells in combination with zoledronic acid and IL-2 to patients with advanced renal cell carcinoma. Cancer Immunol Immunother. 2011 August; 60(8): 1075-1084.
7. Tanaka Y, et al. Expansion of human γ8 T cells for adoptive immunotherapy using a bisphosphonate prodrug. Cancer Sci. 2018 March; 109(3):587-599.

SUMMARY OF THE INVENTION

Problems to be Solved by the Invention

The purpose of the present invention is to provide a method for producing a γδT cell population which express functional TCR or CAR in which γδT cells are prepared in large quantities with high purity and a foreign gene encoding TCR or CAR is efficiently introduced into the obtained γδT cells.

Means for Solving the Problems

The purpose of the present invention is achieved by the following inventions.

(1) A method for producing a γδT cell population expressing a transgene, which comprises Step 1: culturing γδT cells in the presence of one or more compounds selected from the group consisting of tetrakispivaloyloxymethyl ester derivative of 2-(thiazole-2-ylamino) ethylidene-1,1-bisphosphonate, 2-(3-bromopyridine-2-ylamino)ethylidene-1,1-bisphosphonate, 2-(5-fluoropyridine-2-ylamino)ethylidene-1,1-bisphosphonate, 2-(pyrimidine-2-ylamino)ethylidene-1,1-bisphosphonate, 2-(7-azaindole-1-yl)ethylidene-1,1-bisphosphonate, 2-(5-methylthiazole-2-ylamino)ethylidene-1,1-bisphosphonate, 2-(4-phenylthiazole-2-ylamino) ethylidene-1,1-bisphosphonate and 2-(pyrimidin-4-ylamino)ethylidene-1,1-bisphosphonate and a pharmaceutically acceptable salt thereof. Step 2: culturing the γδT cells cultured in step 1 in the presence of IL-7 and IL-15, and Step 3: introducing a gene into the γδT cell cultured in step 2.

(2) A method for producing a γδT cell population expressing a transgene, which comprises Steps 1: culturing γδT cells in the presence of tetrakispivaloyloxymethyl 2-(thiazole-2-ylamino) ethylidene-1,1-bisphosphonate or a pharmaceutically acceptable salt thereof, Step 2: culturing the γδT cells cultured in step 1 in the presence of IL-7 and IL-15, and Step 3: introducing a gene into the γδT cell cultured in step 2.

(3) The method according to (2), wherein the concentration of tetrakispivaloyloxymethyl 2-(thiazole-2-ylamino) ethylidene-1,1-bisphosphonate or a pharmaceutically acceptable salt thereof in step 1 is 0.01 to 1 μM.

(4) The method according to (1) or (2), wherein the γδT cells are derived from a mammal.

(5) The method according to (4), wherein the mammal is a cancer patient or a non-cancer patient.

(6) The method according to (5), wherein the cancer is selected from the group consisting of breast cancer, lung cancer, liver cancer, oral cancer, upper pharyngeal cancer, head cervical cancer, gastric cancer, esophageal cancer, colon cancer, bile duct cancer, malignant melanoma, renal cancer, pancreatic cancer, bile duct cancer, brain tumor, prostate cancer, ovarian cancer, cervical cancer, colorectal cancer, bladder cancer, synovial sarcoma, leukemia, malignant lymphoma and multiple myeloma.

(7) The method according to (1) or (2), wherein the step of introducing a gene in step 3 is characterized by using a DNA vector or an RNA vector.

(8) The method according to (1) or (2), wherein the step of introducing a gene in step 3 is characterized by using a vector selected from the group consisting of a plasmid vector, a lentiviral vector, an adenoviral vector, an adeno-associated virus and a retroviral vector.

(9) The method according to (1) or (2), wherein the step of introducing a gene in step 3 is characterized by using a retroviral vector.

(10) The method according to (1) or (2), wherein the gene is a gene encoding a T cell receptor (TCR) or a chimeric antigen receptor (CAR).

(11) The method of according to (10), wherein the T cell receptor (TCR) is selected from the group consisting of NY-ESO-$1_{p157-165}$/HLA-A2 complex-specific TCR, HTLU-1p40$Tax_{p11-19}$/HLA-A2 complex-specific TCR, HTLU-1p40$Tax_{p301-309}$/HLA-A24 complex-specific TCR and MAGE-A4043-151/HLA-A24 complex-specific TCR.

(12) The method according to (10), wherein the chimeric antigen receptor (CAR) is selected from the group consisting of MAGE-$A4_{p230-239}$/HLA-A2 complex-specific CAR, CEA-specific CAR, GD2-specific CAR, and CD19-specific CAR

(13) The genetically modified γδT cell population obtained by the method according to any one of (1) to (12).

(14) A pharmaceutical composition comprising the genetically modified γδT cell population according to (13) and a pharmaceutically acceptable additive.

(15) The pharmaceutical composition according to (14) for treating a cancer subject by autologous or allogeneic transplantation.

(16) A genetically modified γδT cell population having the characteristics of (i) expressing TCR which specifically recognize NY-ESO-1p157-165/HLA-A2 complex, HTLU-1p40$Tax_{p11-19}$/HLA-A2 complex, HTLU-1p40$Tax_{p301-309}$/HLA-A24 complex or MAGE-A4043-151/HLA-A24 complex, (ii) being positive for CD3 and NKG2D, (iii) producing cytokine and chemokine that contain IFN-γ and TNFα; and (iv) having cellular cytotoxicity.

(17) A genetically modified γδT cell population having the characteristics of (i) expressing CAR which specifically recognize MAGE-$A4_{p230-239}$/HLA-A2 complex, CEA, GD2 or CD19, (ii) being positive for CD3 and NKG2D, (iii) producing cytokine and chemokine that contain IFN-γ and TNFα, and (iv) having cellular cytotoxicity.

(18) The genetically modified γδT cell population according to (16) or (17), characterized in that the genetically modified γδT cell population is a γδT cell population introduced with a gene by using a DNA vector or an RNA vector.

(19) The genetically modified γδT cell population according to (16) or (17), characterized in that the genetically modified γδT cell population is a γδT cell population introduced with a gene by using a vector selected from the group consisting of plasmid vector, lentiviral vector, adenoviral vector, adeno-associated virus and retroviral vector.

(20) The genetically modified γδT cell population according to (16) or (17), characterized in that the genetically modified γδT cell population is a γδT cell population introduced with a gene by using a retroviral vector.

(21) The genetically modified γδT cell population according to (16) or (17), wherein the gene is a gene encoding a T cell receptor (TCR) or a chimeric antigen receptor (CAR).

(22) A pharmaceutical composition comprising the genetically modified γδT cell population according to any one of (16) to (21).

(23) A cell preparation comprising the genetically modified γδT cell population according to any one of (16) to (21).

(24) A genetically modified γδT cell population according to any one of (16) to (21) for treating cancer patients.

(25) An anticancer agent comprising the genetically modified γδT cell population according to any one of (16) to (21).

(26) A method for treating cancer characterized by using the genetically modified γδT cell population according to any one of (16) to (21).

(27) A therapeutic agent for infectious diseases comprising the genetically modified γδT cell population according to any one of (16) to (21).

(28) A method for treating infectious diseases characterized by using the genetically modified γδT cell population according to any one of (16) to (21).

Effect of the Invention

Compared to the conventional method of culturing in the presence of IL-2, according to the present invention, a large number of highly pure γδT cells can be produced by stimulating monocytes obtained from peripheral blood with a bisphosphonic acid ester derivative and then culturing in the presence of IL-7 and IL-15. Further, a foreign gene can be efficiently introduced by using, for example, a retroviral vector to γδT cells proliferated by stimulation of a bisphosphonic acid ester derivative. When TCR and CAR are introduced as a foreign gene, γδT cells in which TCR and CAR are functionally expressed can be obtained.

According to the present invention, even if the amount of blood collected is small, a large amount of γδT cells can be acquired from the collected blood. Besides, a burden on a subject requiring blood collection is reduced. Further, γδT cells having antigen specificity by genetic modification can be sufficiently prepared in a short-term of culture period. The obtained genetically modified γδT cells exhibit strong antitumor effect and does not exhibit a decrease in function due to freezing and thawing, so that cryopreservation is possible. Accordingly, the effective infusion therapy of genetically modified γδT cells can be conducted easily.

BRIEF DESCRIPTION OF THE DRAWINGS

Regarding FIG. 1A-B, peripheral blood monocytes of two healthy subjects (HD1 and HD2) were cultured for 11 days in the presence of tetrakispivaloyloxymethyl 2-(thiazole-2-ylamino) ethylidene-1,1-bisphosphonate (compound 7, 1 μM), IL-7 (25 ng/ml) and IL-15 (25 ng/ml), respectively. The proliferation of γδT cells is shown in the figure. The cell populations at the start of culture (Day 0) and that cultured for 11 days (Day 11) were analyzed by flow cytometry. The γδT cells, which were about several % of the peripheral blood monocytes, proliferated in high purity after the culture, as shown in (A). A culture was started from $3\times10^6$ of peripheral blood monocytes. The number of cells was measured timely. The results are shown in (B). For comparison, in place of IL-7 and IL-15, IL-2 was added (100 IU/mL or 300 IU/mL) to conduct the culture.

Regarding FIG. 2, peripheral blood monocytes of two healthy subjects (HD1 and HD2) were stimulated on Day 0 with compound 7 (1 μM). Then, on Day 4 and Day 5, NY-ESO-1-specific TCR which specifically recognizes the complex of HLA-A2 and NY-ESO-$1_{p157-165}$ peptide (SLLMWITQC) was introduced by using retroviral vector and cultured for 11 days in the presence of IL-7 (25 ng/mL) and IL-15 (25 ng/mL). The figure shows the results obtained by analyzing the expression rate of the introduced TCR in the obtained γδT cells by flow cytometry using a specific tetramer.

Figure 4:
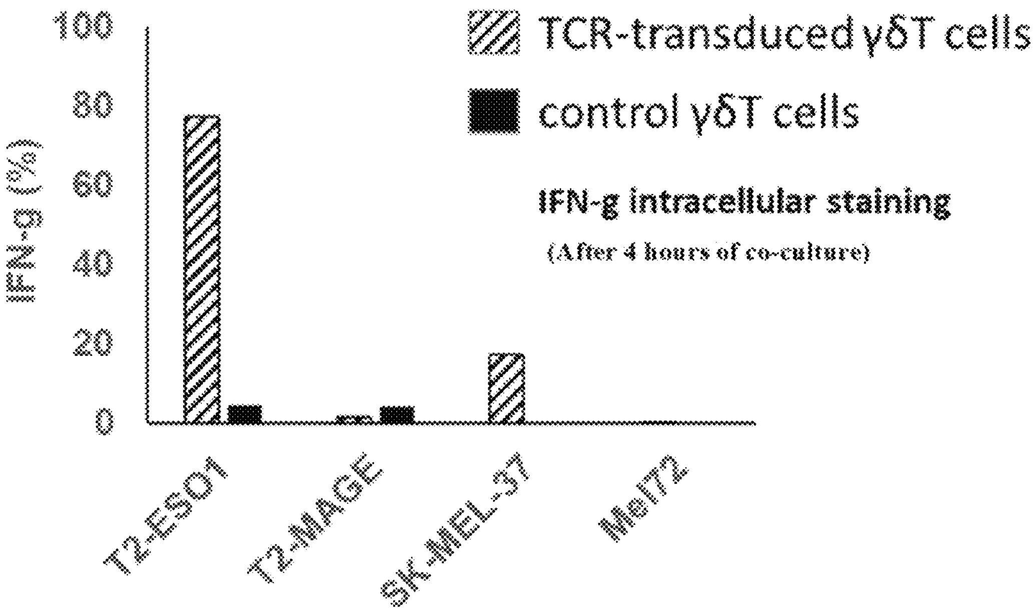

Regarding FIG. 4, γδT cells introduced with NY-ESO-1-specific TCR which specifically recognizes a complex of HLA-A2 and NY-ESO-$1_{p157-165}$ peptide recognized SK-MEL-37, which is HLA-A2 positive NY-ESO-1 antigen positive cell line and produced cytokine IFN-γ. The results are shown in the figure. As a comparison, MEL72, which is HLA-A2 positive NY-ESO-1 antigen negative cell line did not produce cytokines.

Figure 5A:
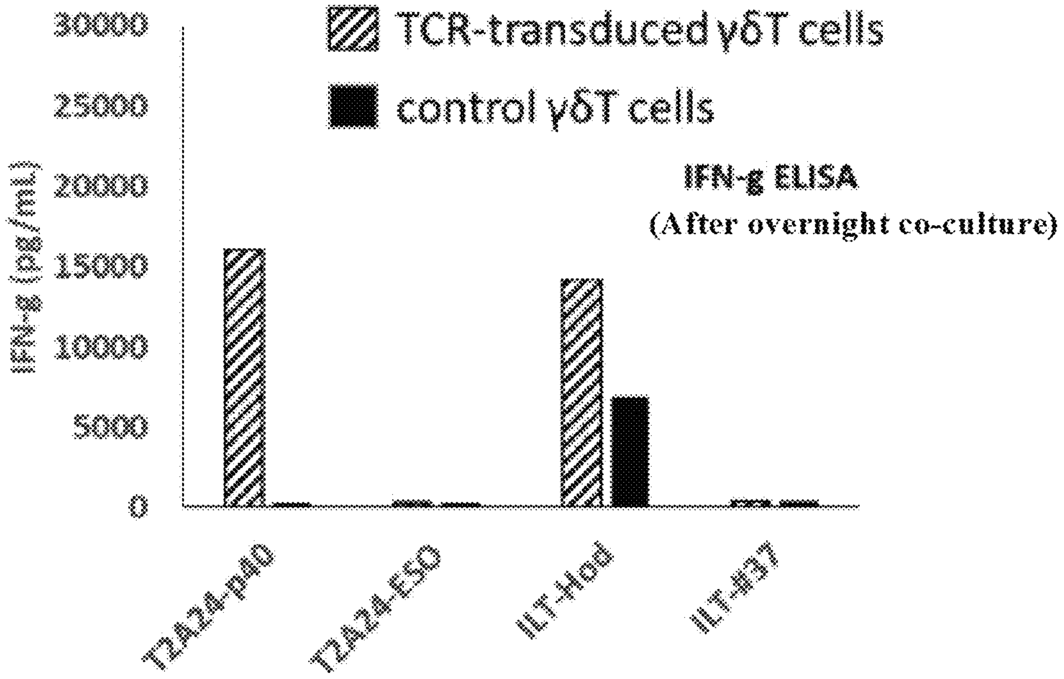

Regarding FIG. 5A, the γ8 T cells introduced with TCR which specifically recognizes a complex of HLA-A24 and HTLV-1 virus antigen p40Tax-derived peptide (SFHSLHLLF) (HTLV-1p40$Tax_{p301-309}$/HLA-A24 complex) did not recognize ILT-#37, which is HLA-A24 negative HTLV-1 positive cell line, but specifically recognized ILT-Hod, which is HLA-A24 positive HTLV-1 positive cell line. FIG. 5A shows the results of measuring the amount of IFN-γ produced. As positive control, an HLA-A24 positive cell line T2A24 (T2A24-p40) added with p40Tax-derived peptide was used; while as negative control, a T2A24 cell line (T2A24-ESO) added with NY-ESO-$1_{p157-165}$ peptide was used.

Figure 5B:
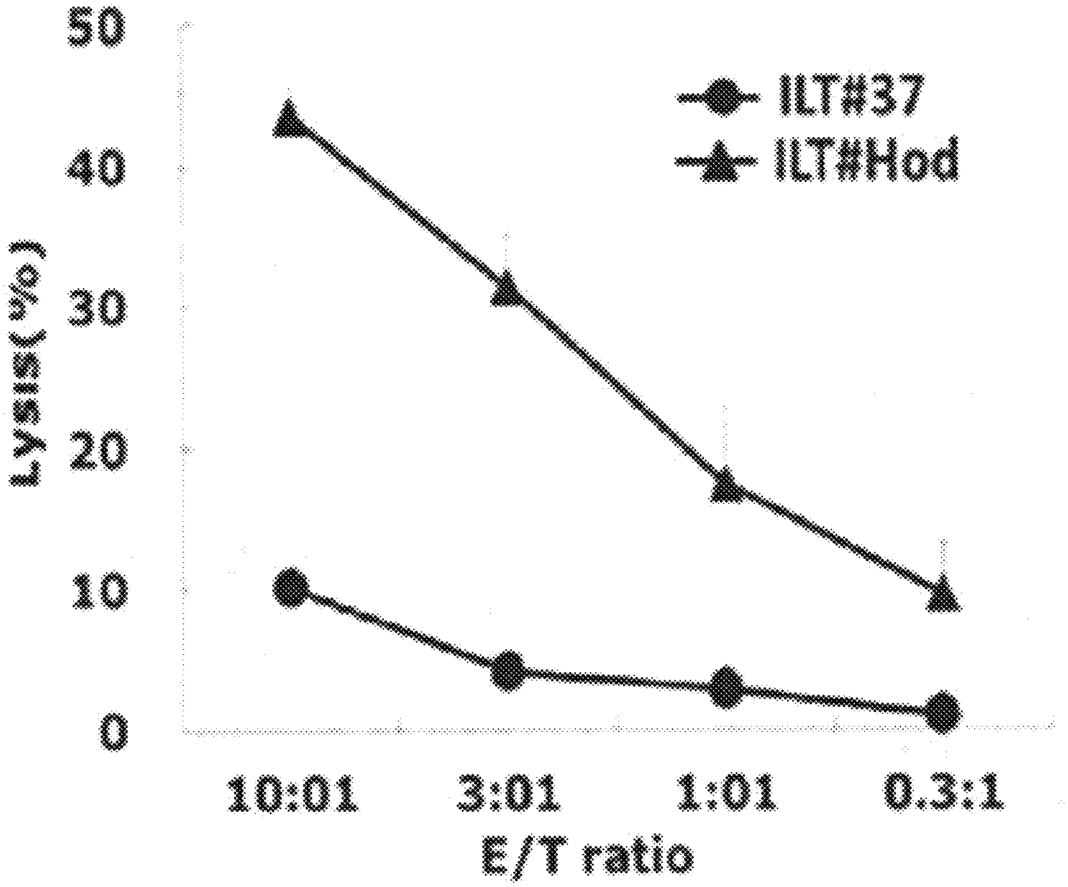

As shown in FIG. 5B, the γδT cells introduced with TCR which specifically recognizes a complex of HLA-A24 and HTLV-1 virus antigen p40Tax-derived peptide (SFHSLHLLF) (HTLV-1p40$Tax_{p301-309}$/HLA-A24 complex) did not recognize ILT-#37, which is HLA-A24 negative HTLV-1 positive cell line, but specifically recognized ILT-Hod, which is HLA-A24 positive HTLV-1 positive cell line. FIG. 5B shows the results of measuring the cytotoxicity. To $1\times10^4$ of ILT-Hod cell lines or ILT-#37 cell lines as target, $1\times10^5$, $3\times10^4$, $1\times10^4$ or $3.3\times10^3$ of γ8 T cells introduced with TCR were added (The E/T ratio was 10:1, 3:1, 1:1 or 0.3:1, respectively.) and co-cultured.

Figure 6:
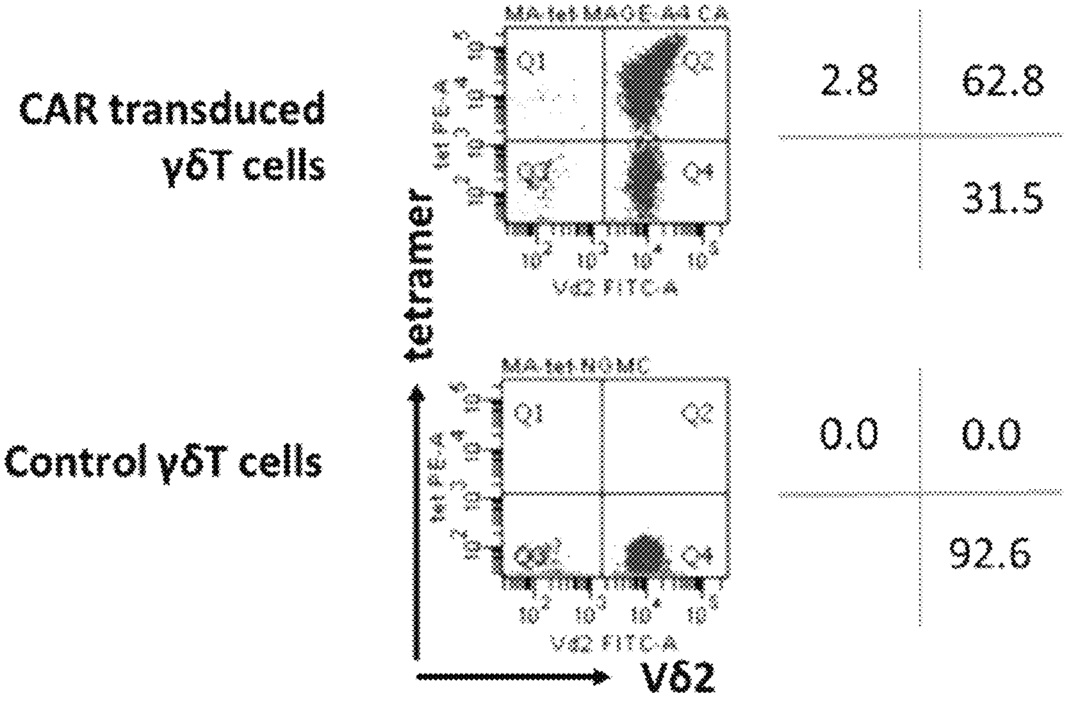

Regarding FIG. 6, healthy human peripheral blood monocytes were stimulated by compound 7 (1 μM) on Day 0. Then, on Day 4 and 5, they were introduced with CAR which specifically recognizes a complex of HLA-A2 and MAGE-$A4_{p230-239}$ peptide (GVYDGREHTV) by using a retroviral vector, and cultured for 11 days in the presence of IL-7 (25 ng/mL) and IL-15 (25 ng/mL). The figure shows the results of analyzing the expression rate of CAR introduced in the obtained γδT cells by flow cytometry using a specific tetramer.

Figure 7:
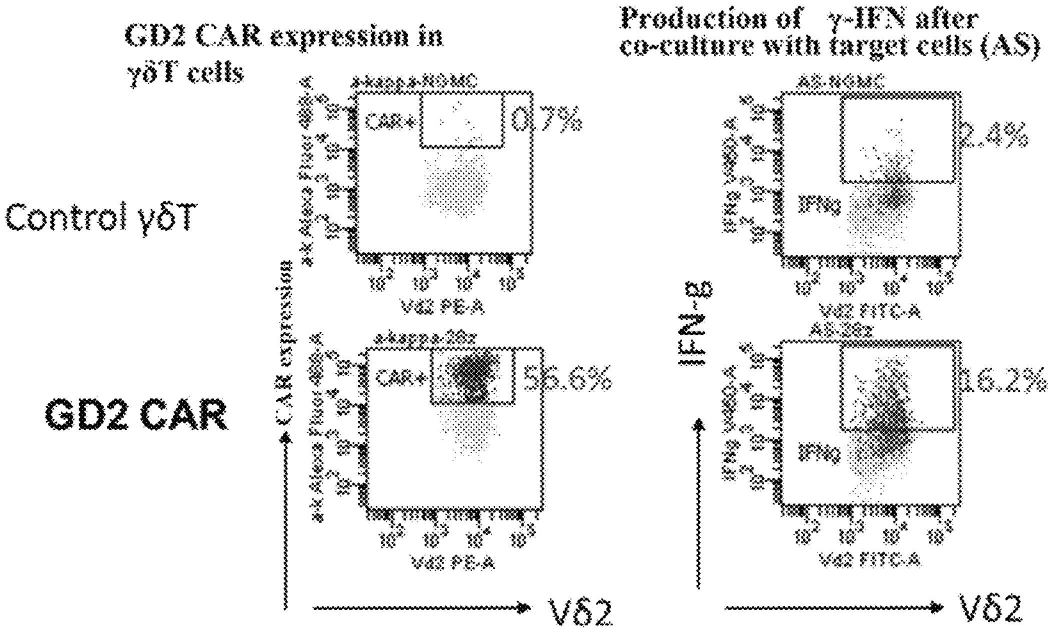

Regarding FIG. 7, healthy human peripheral blood monocytes were stimulated by compound 7 (1 μM) on Day 0. Then, on Day 4 and 5, they were introduced with CAR which specifically recognizes GD2 (disialoganglioside2) by using a retroviral vector, and cultured for 11 days in the presence of IL-7 (25 ng/mL) and IL-15 (25 ng/mL). The expression rate of the introduced CAR in the obtained γδT cells was analyzed by flow cytometry using a specific tetramer. The γδT cells introduced with the GD2-specific CAR gene were co-cultured with AS, which is GD2 positive target tumor cell line, and the production of IFN-γ was analyzed. These results are shown in the FIG. 7. The upper figure shows the results for the control γδT cells, while the lower figure shows the results of the γδT cells introduced with the GD2-specific CAR gene.

Figure 8:
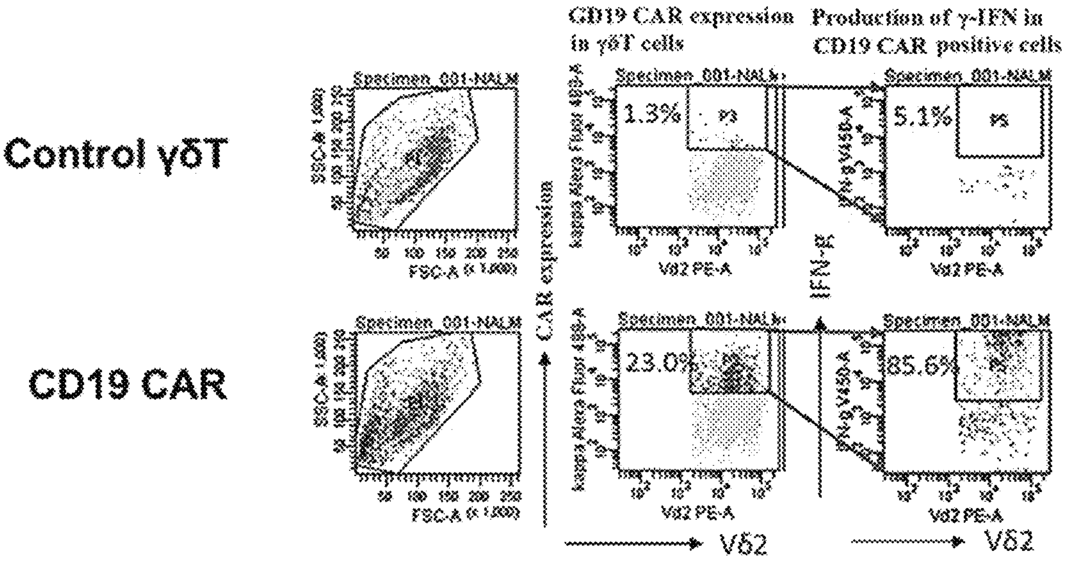

Regarding FIG. 8, healthy human peripheral blood monocytes were stimulated by compound 7 (1 μM) on Day 0. Then, on Day 4 and 5, they were introduced with CAR which specifically recognizes CD19 by using a retroviral vector, and cultured for 11 days in the presence of IL-7 (25 ng/mL) and IL-15 (25 ng/mL). The expression rate of the introduced CAR in the obtained γδT cells was analyzed by flow cytometry using a specific tetramer. The γδT cells introduced with the CD19-specific CAR gene were co-cultured with CD19 positive tumor cells (NALM6), and the production of IFN-γ was analyzed. These results are shown in the FIG. 8. The upper figure shows the results for the control γδT cells, while the lower figure shows the results of the γδT cells introduced with the GD2-specific CAR gene.

Figure 9:
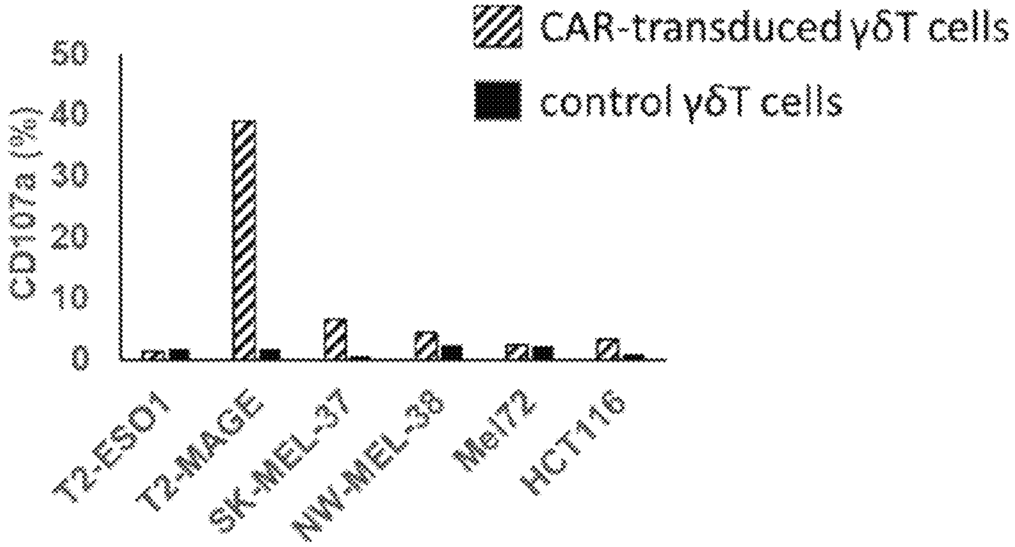

FIG. 9 is a diagram showing that γδT cells introduced with CAR that specifically recognizes a complex of HLA-A2 and MAGE-A4$_{p230\text{-}239}$ peptide (GVYDGREHTV) recognize tumor cell lines in antigen-specific manner and specifically recognize HLA-A2 positive MAGE-A4 positive cell lines (SK-MEL-37 and NW-MEL-38). As positive control, an HLA-A2 positive T2 cell line (T2-MAGE) added with MAGE-A4$_{p230\text{-}239}$ peptide was used; while as negative control, a T2 cell line (T2-ESO1) added with NY-ESO-1$_{p157\text{-}165}$ peptide was used.

Figure 10A:
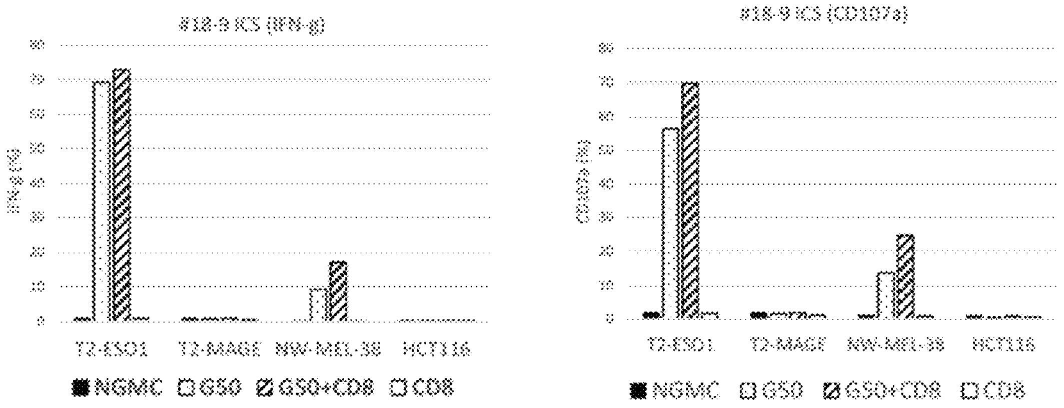

FIG. 10A is a diagram showing tumor-inhibiting effect by γδT cells simultaneously expressing tumor-specific TCR and CD8αβ. FIG. 10A shows the results obtained by co-culturing γδT cells with tumor cells overnight, and measuring the production of IFN-γ and CD107a by intracellular staining (ICS). (B) shows the results obtained by measuring tumor volume to examine the tumor-inhibiting effect by the infusion of γδT cells in which tumor-specific TCR and CD8αβ are simultaneously expressed in a NOG mouse transplanted with tumor cells.

Figure 10B:
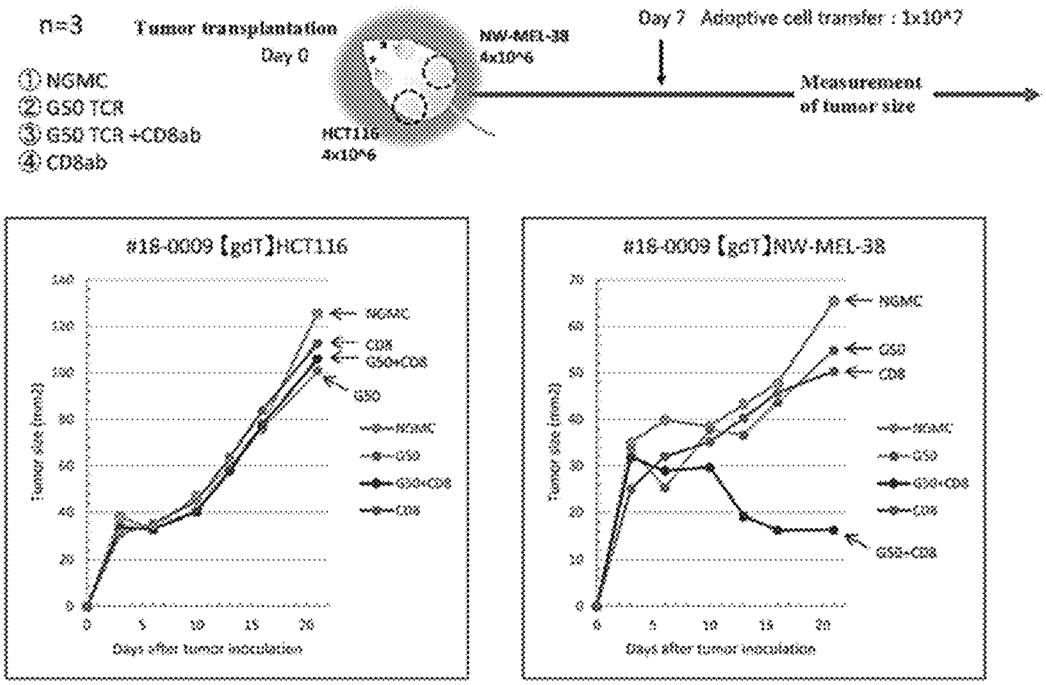

FIG. 10B is a diagram showing tumor-inhibiting effect by γδT cells simultaneously expressing tumor-specific TCR and CD8αβ. FIG. 10B shows the results obtained by measuring tumor volume to examine the tumor-inhibiting effect by the infusion of γδT cells in which tumor specific TCR and CD8αβ are simultaneously expressed in a NOG mouse transplanted with tumor cells.

Figure 11A:
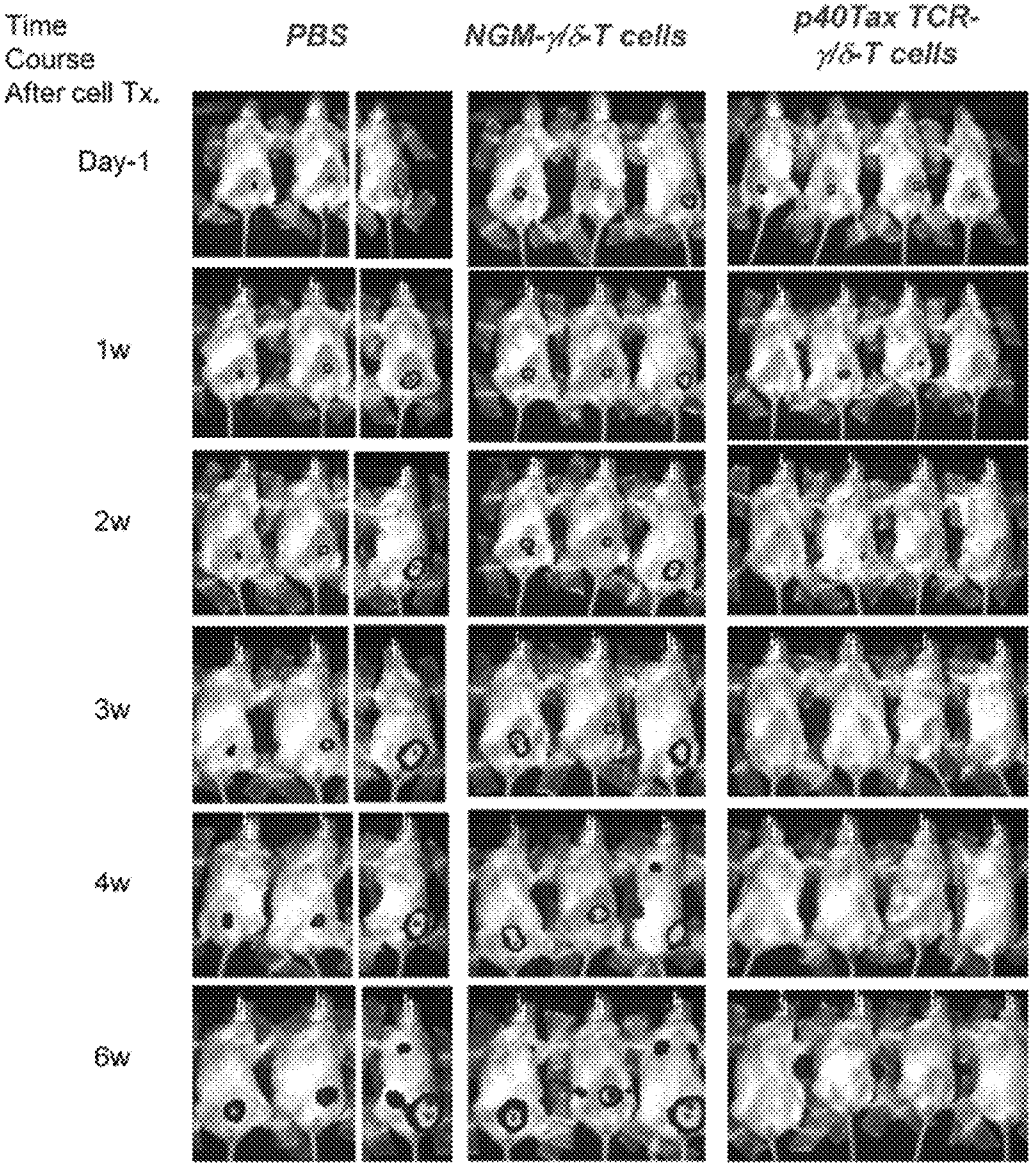

FIG. 11A is a diagram showing tumor-inhibiting effect by γδT cells introduced with tumor-specific TCR. FIG. 11A is a diagram showing visualized results of tumor formation in a NOG mouse by bio-imaging.

Figure 11B:
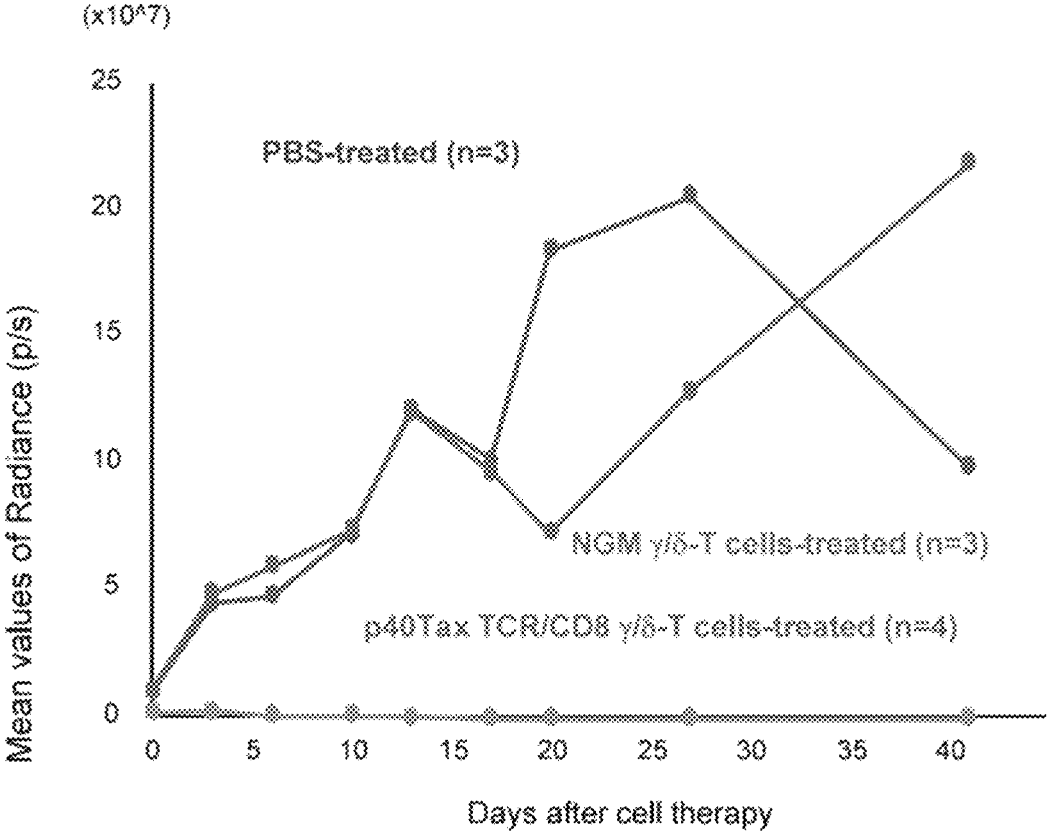

FIG. 11B is a diagram showing tumor-inhibiting effect by γδT cells introduced with tumor-specific TCR. FIG. 11B is a diagram showing the tumor formation in a NOG mouse with average radiance.

Figure 12:
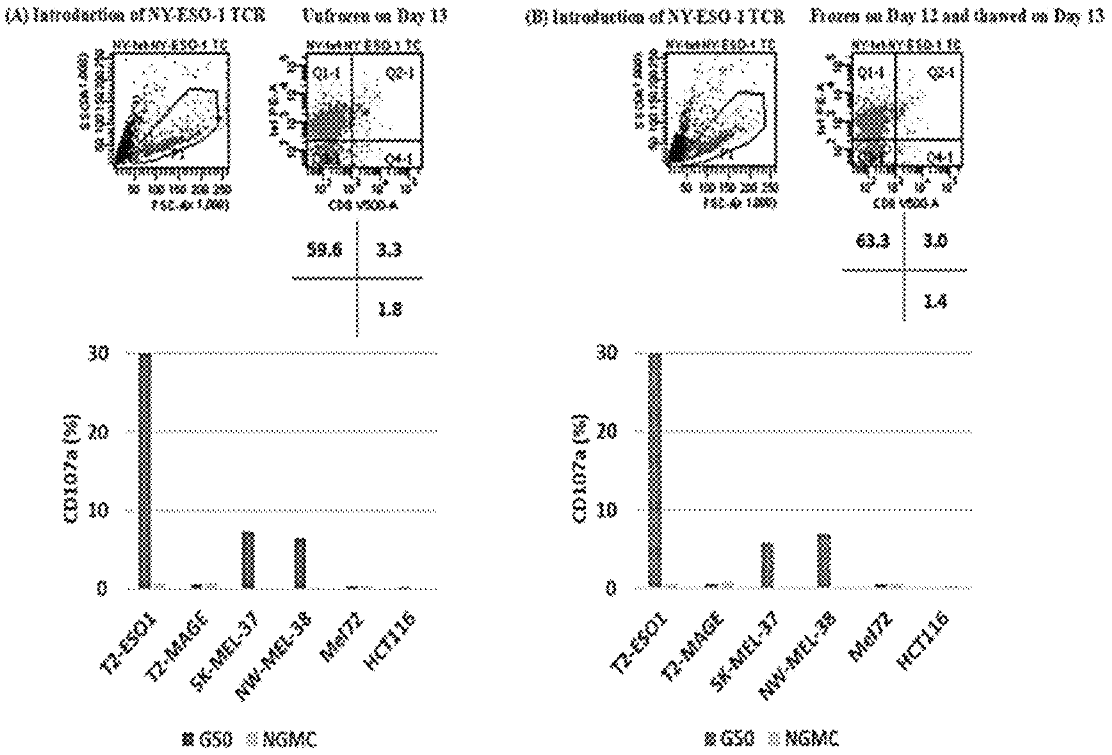

FIG. 12 is a diagram showing a result of analyzing the effect of freezing and thawing on the function of genetically modified γδT cells stimulated by compound 7. (A) is a diagram showing a result of unfrozen cells. (B) is a diagram showing a result of frozen and thawed cells.

Figure 13A:
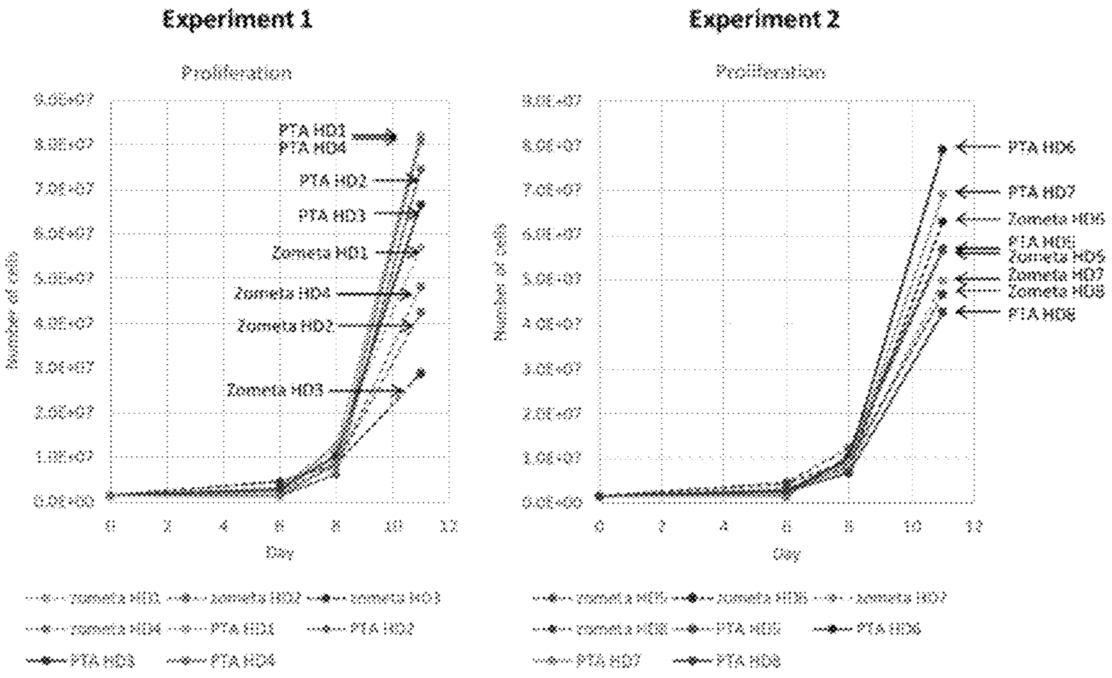

FIG. 13A is a diagram showing a result of comparing the effect of compound 7 with that of zoledronic acid on the proliferation of γδT cells. FIG. 13A is a diagram showing the effect on the peripheral blood monocytes obtained from corresponding subjects.

Figure 13B:
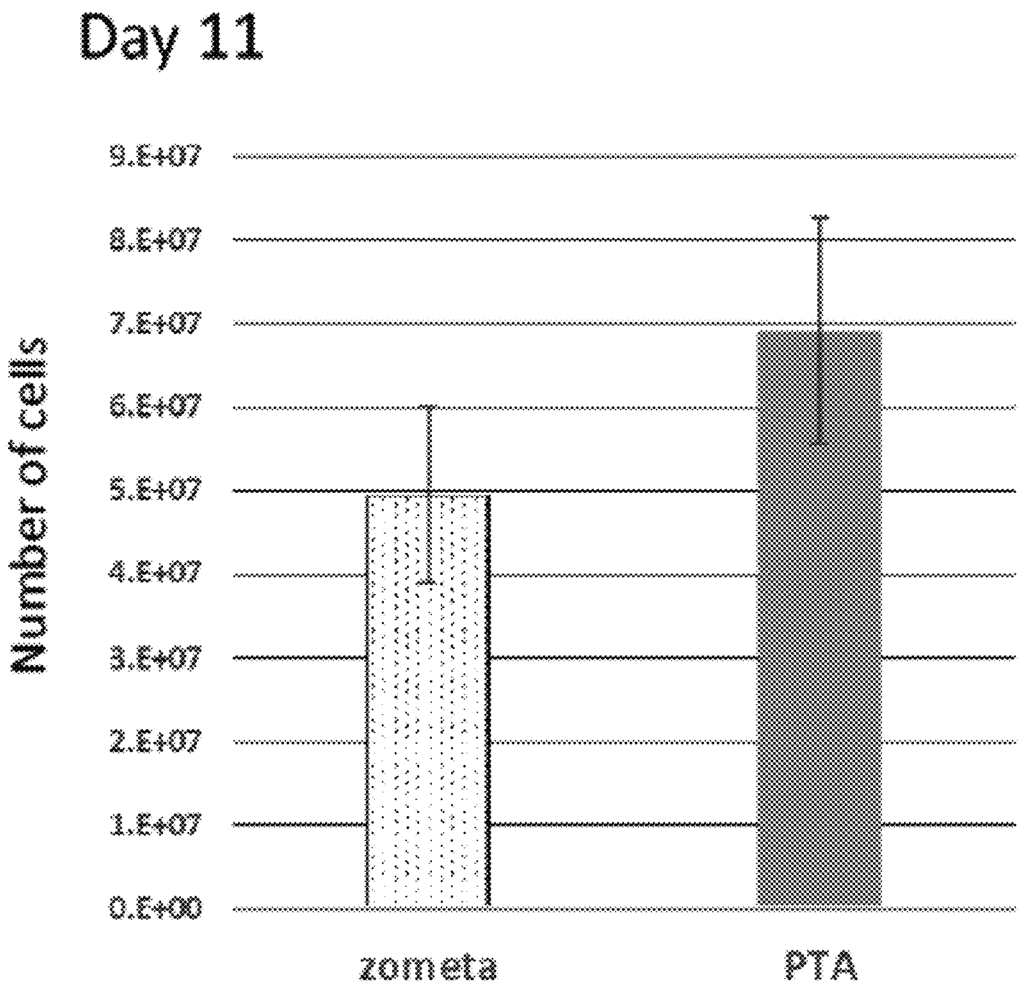

FIG. 13B is a diagram showing a result of comparing the effect of compound 7 with that of zoledronic acid on the proliferation of γδT cells. FIG. 13B is a diagram showing average values.

FIG. 14A-B is a diagram showing a result of comparing the effect of compound 7 on the purity of γδT cells with zoledronic acid. (A) is a diagram showing the frequency of the γδT cells in CD3 positive cells (Vd2/CD3). (B) is a diagram showing the frequency of the γδT cells in lymphocyte fraction (P1) (Vd2/P1).

EMBODIMENTS TO CARRY OUT THE INVENTION

[Bisphosphonic Acid Ester Derivatives]

Bisphosphonic acid is an analog of phosphoric acid. It is a compound (P—C—P) wherein O (oxygen atom) in the phosphate skeleton P—O—P is substituted by C (carbon atom). The nitrogen-containing bisphosphonic acid is a compound having N (nitrogen atom) in the bisphosphonic acid molecule. The bisphosphonic acid ester derivatives used in the present invention are pivaloyloxymethyl (POM) ester of the nitrogen-containing bisphosphonic acid described in Table 1, or a pharmaceutically acceptable salt, hydrate or solvate thereof. These compounds are described in patent document 1 (WO 2016/098904). They can be produced according to the description. However, they can also be synthesized by using a synthetic method well known to those skilled in the art.

TABLE 1

| Number of compound | Structure | Name |
| --- | --- | --- |
| 7 | 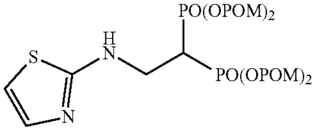 | tetrakispivaloyloxymethyl 2-(thiazole-2-ylamino)ethylidene-1,1-bisphosphonate |
| 2 | 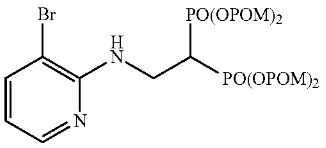 | tetrakispivaloyloxymethyl 2-(3-bromopyridine-2-ylamino) ethylidene-1,1-bisphosphonate |
| 5 | 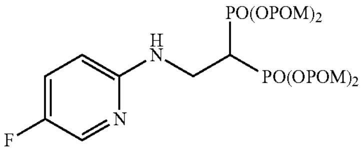 | tetrakispivaloyloxymethyl 2-(5-fluoropyridine-2-ylamino) ethylidene-1,1-bisphosphonate |

TABLE 1-continued

| Number of compound | Structure | Name |
|---|---|---|
| 6 | 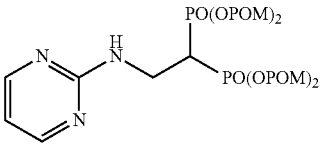 | tetrakispivaloyloxymethyl 2-(pyrimidine-2-ylamino) ethylidene-1,1-bisphosphonate |
| 31 | 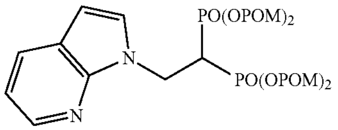 | tetrakispivaloyloxymethyl 2-(7-azaindole-1-yl)ethylidene-1,1-bisphosphonate |
| 34 | 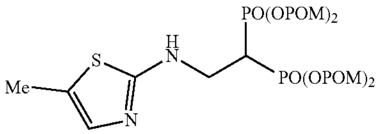 | tetrakispivaloyloxymethyl 2-(5-methylthiazole-2-ylamino) ethylidene-1,1-bisphosphonate |
| 35 | 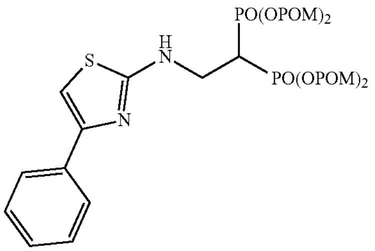 | tetrakispivaloyloxymethyl 2-(4-phenylthiazole-2-ylamino) ethylidene-1,1-bisphosphonate |
| 39 | 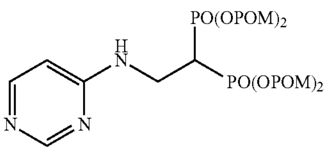 | tetrakispivaloyloxymethyl 2-(pyrimidin-4-ylamino)ethylidene-1,1-bisphosphonate |

The γδT cells can be cultured in the presence of one or more compounds of the nitrogen-containing bisphosphonic acid pivaloyloxymethyl esters described in Table 1. However, it is preferable to use a tetrakispivaloyloxymethyl 2-(thiazole-2-ylamino) ethylidene-1,1-bisphosphonate (compound 7) or a pharmaceutically acceptable salt thereof. A pharmaceutically acceptable salt is generally acceptable salt from the viewpoints of pharmacology and pharmaceutics. Moreover, it does not exhibit toxicity to cells even when added to a culture solution of the cells.

A nitrogen-containing bisphosphonic acid, such as zoledroic acid used as a bone resorption inhibitor, inhibits farnesyl diphosphate synthase (FDPS) in cells (van Beek E, et al. Biochem Biophys Res Commun. 1999 Oct. 14; 264 (1):108-111). The inhibition of FDPS by the nitrogen-containing bisphosphonic acid increases the level of isopentenyl diphosphate which is the upstream metabolite of FDPS in the biosynthetic pathway, and stimulates γδT cells as a result (Wang H, J Immunol. 2011 Nov. 15; 187 (10):5099-5113 and Tanaka Y, Sci Rep. 2017 Jul. 20; 7(1):5987). When a compound described in Table 1 of the specification is incorporated into cells, the pivaloyloxymethyl group is subjected to hydrolysis by esterase in the cells to be released, and turns into a free acid. The free acid inhibits FDPS in the γδT cells and stimulates the γδT cells as a result (patent document 1, non-patent document 7, and Tanaka Y, Sci Rep. 2017 Jul. 20; 7(1):5987).

The nitrogen-containing bisphosphonic acid has low permeability into cells in the state of free acid. The compounds described in Table 1 of the present specification are pivaloyloxymethyl (POM) esters, and imparted with permeability to cells. The compounds described in Table 1 are preferably substituted with four POM groups per molecule. However, they may be substituted by one to three POM groups per molecule of nitrogen-containing bisphosphonic acid as long as the permeability into the cells is maintained. Further, as long as the permeability to the cells is maintained and that they can be hydrolyzed by esterase in the cells, other esters may also be used. N-butyloxymethyl ester derivatives and n-heptyloxymethyl ester derivatives are exemplified. These nitrogen-containing bisphosphonic acid ester derivatives may preferably have one to four ester groups, preferably four ester groups per molecule.

[Culture of γδT Cells]

The γδT cells used in the present invention are derived from monocytes separated from a biopsy tissue of peripheral blood, umbilical cord blood, or a cancer tissue of a mammal, particularly a cancer patient or a non-cancer patient. The γδT cells are preferably obtained from whole blood by a density centrifugal separation method well known to a person skilled in the art. The density centrifugal separation method includes, but is not limited to, a method using a lymphocyte separation solution, such as Ficoll, Lymphoprep® or the like. Furthermore, the cells may be separated by the methods of FACS (fluorescence-activated cell sorting) or MACS (magnetic-activated cell sorting).

The examples of cancer species of cancer patients for collecting monocytes include, but not limited thereto, breast cancer, lung cancer, liver cancer, oral cancer, upper pharyngeal cancer, head cervical cancer, gastric cancer, esophageal cancer, colon cancer, skin cancer, malignant melanoma, renal cancer, pancreatic cancer, brain tumor, prostate cancer, ovarian cancer, cervical cancer, colorectal cancer, bladder cancer, synovial sarcoma, fat sarcoma, leukemia, malignant lymphoma, and multiple myeloma.

The γδT cells can be proliferated from peripheral blood monocytes, umbilical cord blood monocytes or tissue-derived monocytes by culturing with a cell culture solution containing a nitrogen-containing bisphosphonic acid POM ester compound described in Table 1 of the specification as well as IL-7 and IL-15. Those IL-7 and IL-15 which are each mutant or fragment, and are bound to respective receptors to exhibit biological activity, are within the scope of the present invention. The cell culture solution includes, but is not limited to, RPMI 1640 culture solution, Yssel culture solution and the like. To a cell culture solution, for example, bovine fetal calf serum, human AB serum, autologous plasma, human albumin, and serum substitute can be added in an amount of 0.1 to 20% (v/v). The nitrogen-containing bisphosphonic acid POM ester can be added to a cell culture solution at a concentration of 0.01 to 1 μM. Regarding IL-7 and IL-15, their concentration to be added to a cell culture solution can be changed according to the specific activity of the lot to be used. However, either of the cytokine can be added at a concentration of 5 to 100 ng/mL.

The γδT cells are stimulated by culturing in an environment of 5% $CO_2$ and 37° C. for 1 to 7 days in the presence of a nitrogen-containing bisphosphonic acid POM ester. IL-7 and IL-15 may be added to a culture solution simultaneously with the nitrogen-containing bisphosphonic acid POM ester or may be added 1 to 5 days after the addition of the bisphosphonic acid POM ester.

[Introduction of a Gene into γδT Cells]

Monocytes derived from peripheral blood or tissue are cultured in the presence of a nitrogen-containing bisphosphonic acid POM ester, IL-7 and IL-15. The obtained γδT cells can be introduced with genes using a gene transfer method well known to those skilled in the art. Introduction of a gene can be carried out at any point of the culture period of the γδT cells. However, it is preferable to carry out the introduction at a point from the next day to 14 days after the start of the culture. The methods for introducing genes into the γδT cells include lipofection method, calcium phosphate co-precipitation method, DEAE-dextran method, electroporation method, microinjection method, plasmid vector method, viral vector method, and the like. A DNA vector or an RNA vector is used as the vector. A lentiviral vector, an adenoviral vector, an adeno-associated virus, and a retroviral vector can be exemplified as the viral vectors. However, a retroviral vector is preferable.

When introducing genes into γδT cells by using a viral vector, a functional substance capable of improving viral infection efficiency can be used. For example, functional substances having activity to bind to a viral vector such as fibronectin, fibronectin fragment, polypeptide or the like can be exemplified. Especially in the case of a retroviral vector, it is preferable to use Retronectin® or Vecofusin-1® which are fibronectin fragment having a heparin binding site. These functional substances can be used in a state of being fixed to a suitable solid phase (such as, a plate, a dish, a conical tube, a microtube, etc.) or a carrier (micro-beads or the like).

Examples of genes to be introduced into the γδT cells include, but are not limited to, NY-ESO-1-specific TCR, HTLV-1 Tax-specific TCR, MAGE-A4-specific TCR, MAGE-A4-specific CAR, CEA-specific CAR, GD2-specific CAR, and CD19-specific CAR. The structure of retroviral vector for TCR expression is a structure in which an α-chain gene and a β-chain gene of each specific TCR are incorporated between the LTRs at both ends which contain enhancer and promoter (Long Terminal Repeat). The structure of retroviral vector for CAR expression is a structure in which a leader sequence, VH and VL, which are components of an antibody specifically recognizing the complex of HLA-A2 and MAGE-$A4_{p230-239}$ peptide, and CL, CD28TM and intracellular domain are incorporated continuously between the LTRs at both ends which contain enhancer and promoter. In order to express and introduce individual TCR and CAR, other means may be used, such as using a lentiviral vector.

After gene introduction into γδT cells by using vectors, the gene expression of the cells can be confirmed by a method known to a person skilled in the art such as flow cytometry, RT-PCR, Northern blotting, Western blotting, ELISA, fluorescent immunostaining, and the like.

The γδT cells introduced with TCR gene or CAR gene express the corresponding TCR or CAR on cell membrane. When the specific antigen recognized by these TCR and CAR binds to TCR and CAR respectively, genetically modified γδT cells are activated. Production of cytokine such as interferon-γ (IFN-γ) and tumor necrosis factor α (TNFα) and expression of molecules of cellular cytotoxicity such as CD107a are observed.

The genetically modified γδT cells thus obtained exhibit specific cytotoxic properties to cells expressing antigens specifically recognized by TCR or CAR expressing the cells. Therefore, the genetically modified γδT cell population can be administered to a patient for treatment or prevention of diseases associated with cells expressing the antigen such as viral infections, bacterial infections, fungal infections, protozoa infections, or cancer. The administration to a patient is preferably injection or infusion. As the route of administration, intravenous administration is preferred. However, it may be administered by direct injection into a biological tissue. Besides, since GVHD (graft-versus-host disease) is not induced, it is not limited to autologous transplantation. Allogeneic transplantation is also possible.

When the antigen is a cancer-specific antigen, a cell preparation or a pharmaceutical composition containing the genetically modified γδT cell population of the present invention can be used as an anticancer agent. Examples of the cancer-specific antigen include NY-ESO-1, MAGE-A4, CEA (cancer fetal antigen), and the like. As the cancer species expressing these cancer-specific antigens, for example, breast cancer, lung cancer, gastric cancer, esophageal cancer, bile duct cancer, malignant melanoma, prostate cancer, ovarian cancer, synovial sarcoma, fat sarcoma and multiple myeloma are exemplified. The CD19 expressed in the B-cell is used as an antigen, and the anticancer agent against the B-cell tumor can be used. As the cancer-specific antigen, GD2 (disialoganglioside 2) can be exemplified. The GD2 expressed in neuroblastoma is not only neuroblastoma but also widely expressed in malignant tumors originating from other neuroectoderm such as brain tumors, retinal fibroblasts, lung small cell carcinoma and malignant melanoma. The pharmaceutical composition of the present invention can be used for the treatment or prevention of these cancer. When the antigen is an infectious disease-specific antigen, a cell preparation or a pharmaceutical composition containing the genetically modified γδT cell population of the present invention can be used as a therapeutic agent for neoplastic disease caused by infectious diseases or an infectious disease. Examples of the infectious disease-specific antigen include HTLV-1 (human T cell leukemia virus type 1)-derived antigen Tax and the like. The infectious disease or the neoplastic disease expressing these infectious disease-specific antigens includes, for example, HTLV-1-related spinal cord, HTLV-1-grape membrane flame, ATL (adult T cell leukemia lymphoma). The pharmaceutical composition of the present invention can be used for the treatment or prevention of these infectious diseases.

The cell preparation or pharmaceutical composition of the present invention may contain a pharmaceutically acceptable additive. Examples of the additive include cell culture solution, phosphate buffered saline, and the like.

EXAMPLES

The present invention will be described in detail with reference to the examples. However, the present invention is not limited thereto.

Example 1

[Proliferation of γδT Cells]

Figure 1A:
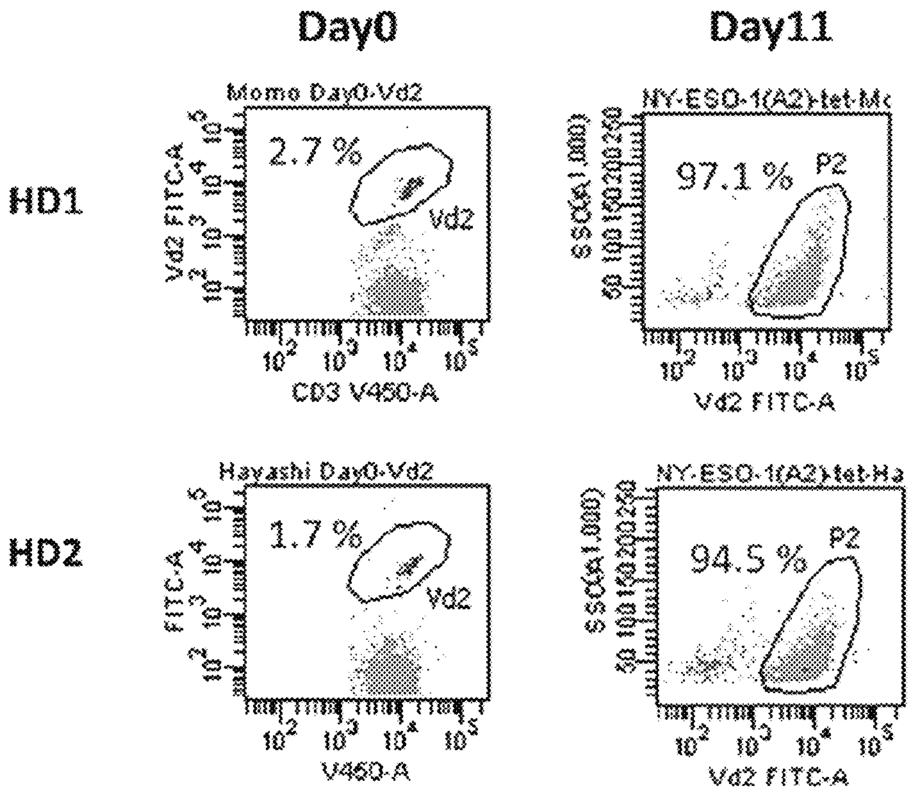

The monocytes were prepared from peripheral blood of two healthy subjects by Ficoll. Personal agreement for the blood collection was achieved based on the research ethics code of the medical school of Mie University. The monocytes adjusted to $1.5\times10^6$ cells/mL with the culture solution of Yssel containing 10% human AB serum were cultured for one day in the presence of tetrakispivaloyloxymethyl 2-(thiazole-2-ylamino) ethylidene-1,1-bisphosphonate (compound 7, 1 μM), and then added with 25 ng/mL of IL-7 (Miltenyi Biotec, catalog number: 170-076-111) and 25 ng/mL of IL-15 (Miltenyi Biotec, catalog number: 170-076-114), and further cultured for 10 days. The frequency of the γδT cells in the monocyte population were analyzed by flow cytometry (FACSCANTO II, Becton Dickinson). As a result, the ratio of the γδT cells at the start of culture (Day 0) was 2.7% for donor 1 (HD1) and 1.7% for donor 2 (HD2), respectively. By culturing in the presence of compound 7, IL-7 and IL-15, the ratio turned to 97.1% and 94.5%, respectively on Day 11, and most of the cells proliferated with high purity into γδT cells (FIG. 1A). Peripheral blood of healthy human normally contains 1 to 3% of the γδT cells. However, approximately $1\times10^8$ of γδT cell populations could be prepared in high-purity from 1.5 mL of peripheral blood.

Figure 1B:
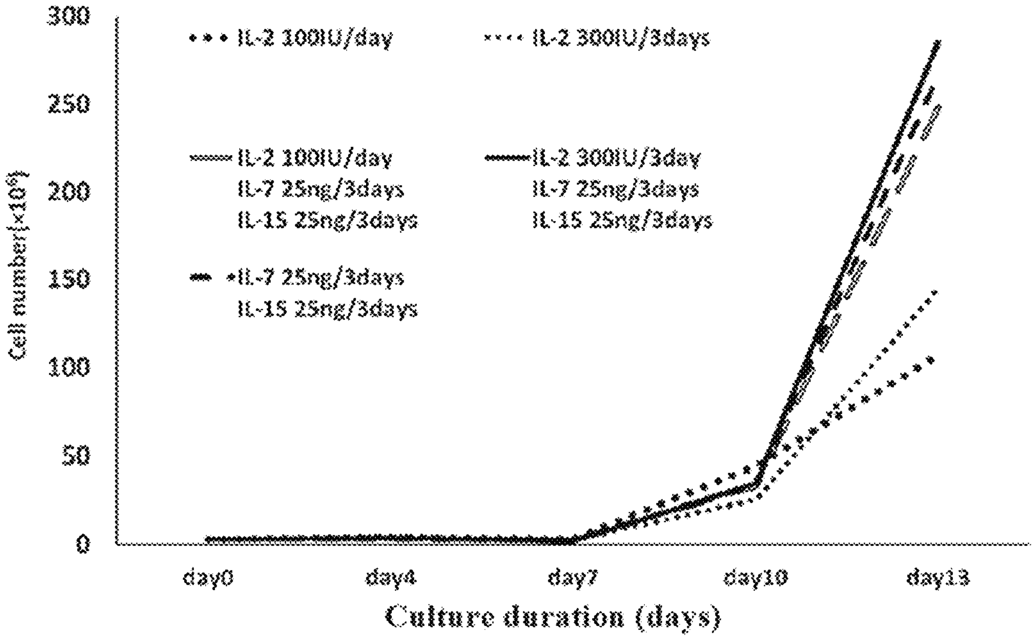

$3\times10^6$ of monocytes collected from 3 mL of peripheral blood were cultured up to Day 13 in the presence of compound 7 (1 μM), IL-7 (25 ng/mL) and IL-15 (25 ng/mL). A culture solution of Yssel containing 10% human AB serum was used as the culture solution. As a result, rapid cell proliferation was observed from about Day 8 after the culture. The number of cells on Day 13 was $3\times10^8$, which was about 5000 times (FIG. 1B). It is shown that a γδT cell population of high-purity can be proliferated with high efficiency by stimulating and proliferating γδT cells with compound 7 and culturing using a culture solution containing IL-7 and IL-15.

As comparison, IL-7 and IL-15 in the culture solution were replaced by IL-2 (PROLEUKIN, Chiron Therapeutics), and monocytes were cultured. As a result, it is shown that the effect of promoting cell proliferation by IL-7 and IL-15 is superior to that by IL-2 (100 IU/mL and 300 IU/mL) alone (FIG. 1B). Further, the effect of promoting cell proliferation by IL-7 and IL-15 is not further increased by further addition of IL-2.

Example 2

[Production of a γδT Cell Population Introduced with a Foreign Gene (TCR)]

Figure 2:
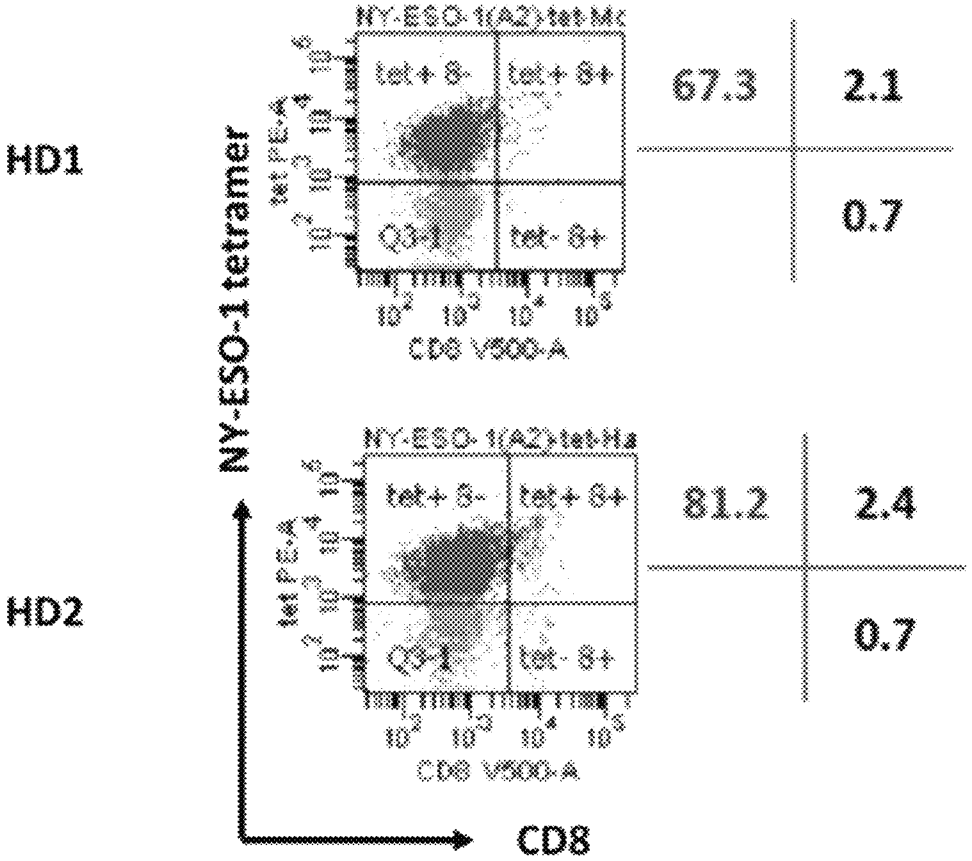

On Day 0, $1.5\times10^6$ monocytes collected from 1.5 mL of peripheral blood of healthy human were stimulated and cultured in the presence of compound of 7 (1 μM). On Day 1, IL-7 and IL-15 were added to the culture solution to make the final concentration of 25 ng/mL, respectively. On Day 4 and Day 5, infection introduction was performed by using a retroviral vector for NY-ESO-1-specific TCR expression which specifically recognizes a complex of HLA-A2 and NY-ESO-$1_{p157-165}$ peptide (SLLMWITQC) in the presence of Retronectin® (Takara Bio Inc.). Thereafter, the culture was continued by a culture solution containing IL-7 and IL-15. On Day 11, the expression efficiency of the introduced TCR was examined. The results are shown in FIG. 2. It is shown by FIG. 2 that γδT cells introduced with a TCR gene was obtained with high efficiency. The obtained γδT cells were positive for CD3 which forms a complex with TCR and receptor NKG2D (natural-killer group 2, member D).

Figure 3:
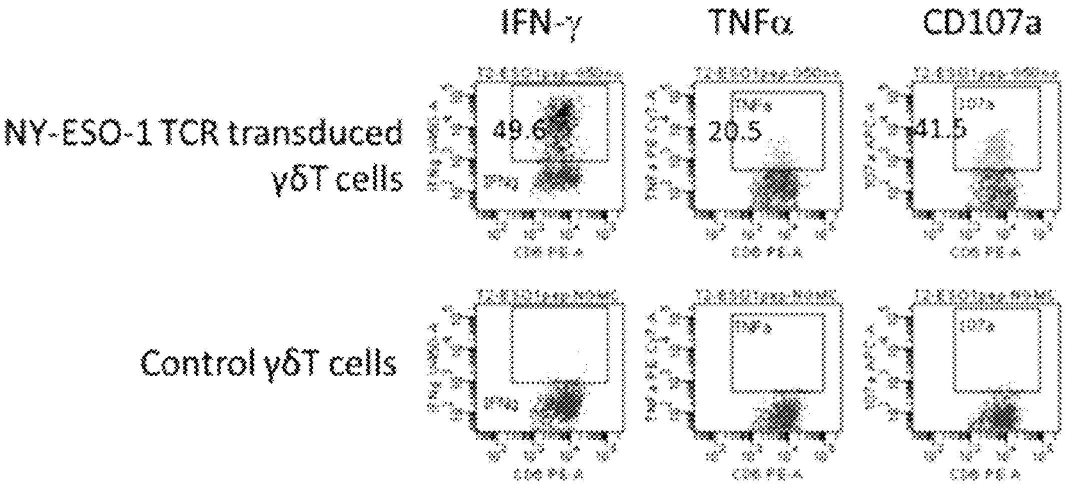
FIG. 3 shows results obtained by measuring cytokine (IFN-γ and TNFα) production by γδT cells introduced with NY-ESO-1-specific TCR and CD107a expression. Cells obtained by adding NY-ESO-$1_{p157-165}$ peptide to HLA-A2 positive T2 cell lines were used as target cells. As a result, it is shown that the γδT cells introduced with TCR express IFN-γ, TNFα and CD107a in antigen-specific manner.

It is confirmed that the γδT cells introduced with the TCR by NY-ESO-1-specific TCR expression retroviral vector produces cytokines IFN-γ and TNFα by co-culture (4 hours) with HLA-A2 positive cell line T2 added with NY-ESO-$1_{p157-165}$ (SLLMWITQC) peptide, and expresses CD107a as an index of functional cellular cytotoxicity (FIG. 3). The amino acid in the amino acid sequence is described by one character notation.

Example 3

[Recognition of an Antigen-Specific Tumor Cell Line by γδT Cells Introduced with a TCR Gene]

Tumor recognition of γδT cells introduced with TCR genes which recognize NY-ESO-$1_{p157-165}$ peptide specifically in the restriction of HLA-A*02:01 was examined. The results are shown in FIG. 4. The production of IFN-γ was confirmed by intracellular cytokine staining using intracellular IFN-γ staining method when SK-MEL-37 cell line which is NY-ESO-1 positive HLA-A*02:01 positive cell line and the γδT cells were co-cultured (4 hours). However, no production of IFN-γ was observed in the co-culture with Mel 72 which is NY-ESO-1 negative HLA-A*02:01 positive cell line. As positive control, an HLA-A2 positive T2 cell line (T2-ESO1) added with NY-ESO-$1_{p157-165}$ peptide was used. While as negative control, a T2 cell line (T2-MAGE) added with MAGE-$A4_{p230-239}$ peptide was used. It was shown that the TCR-introduced γδT cells produced were functional and recognized tumor cells antigen-specifically.

Example 4

[Recognition of HLA-A*24:02 and p40Tax Positive Cell Line by γ8 T Cells Introduced with HTLV-1 Virus Antigen p40Tax-Specific TCR]

Antigen recognition of γδT cells introduced with a TCR which recognizes HTLV-1 virus antigen p40Tax-derived peptide (SFHSLHLLF) specifically in the restriction of HLA-A*24:02 was examined by using a retroviral vector. The results are shown in FIG. 5. When ILT-Hod cell lines which is HLA-A*24:02 positive HTLV-1 positive cell lines and the γδT cells were co-cultured (18 hours), IFN-γ production in the culture supernatant was confirmed by an ELISA method. However, in the co-culture with ILT-#37 cell lines which is HLA-A*24:02 negative HTLV-1 positive cell line, IFN-γ production was not observed (FIG. 5A). As positive control, HLA-A24 positive T2A24 cell line (T2A24-p40) added with a p40Tax-derived peptide was used. While as negative control, T2A24 cell line (T2A24-ESO) added with NY-ESO-$1_{p157-165}$ peptide was used. Further, when the cell number ratio of the γδT cells to the ILT-Hod cell line or the ILT-#37 cell line was changed and co-cultured, strong cytotoxicity against the ILT-Hod cell line depending on the E/T ratio was observed (FIG. 5B). Accordingly, it was shown that the γδT cells introduced with TCR produced from the γδT cells stimulated by compound 7 were functional, and that they recognized and damaged the tumor cells antigen-specifically.

Example 5

[Production of a γδT Cell Population Introduced with a Foreign Gene (CAR)]

In recent years, CAR therapy for a blood-based tumor using a CAR gene has been clinically applied. Therefore, it is examined whether or not CAR can be introduced into the γδT cells. On Day 0, $1.5\times10^6$ of monocytes collected from 1.5 mL of peripheral blood of healthy human were stimulated and cultured in the presence of compound 7 (1 μM). On Day 1, IL-7 and IL-15 were added to the culture solution to make the final concentration of 25 ng/mL, respectively. On Day 4 and Day 5, infection introduction was performed by using a retroviral vector for CAR expression which specifically recognizes a complex of HLA-A*02:01 and MAGE-$A4_{p230-239}$ peptide (GVYDGREHTV) in the presence of retronectin. Thereafter, the culture was continued by a culture solution containing IL-7 and IL-15. On Day 11, the expression efficiency of the introduced CAR was examined.

The results are shown in FIG. 6. It is shown by FIG. 6 that γδT cells introduced with CAR genes was obtained with high efficiency. The obtained γδT cells were positive for CD3 and NKG2D.

Similarly, on Day 4 and Day 5, infection introduction was performed by using a retroviral vector for CAR expression which specifically recognizes GD2 (disialoganglioside2) or CD19 in the presence of retronectin. Thereafter, the culture was continued by a culture solution containing IL-7 and IL-15. On Day 11, the expression efficiency of the introduced CAR was examined.

As a result, the expression of GD2-specific CAR when a CAR gene which specifically recognizes GD2 was introduced is shown in FIG. 7. The expression of CD19-specific CAR when a CAR gene which specifically recognizes CD19 was introduced is shown in FIG. 8. It is shown by FIGS. 7 and 8 that γδT cells introduced with CAR genes targeting GD2 or CD19 was obtained with high efficiency compared to the control. When the γδT cells introduced with a GD2-specific CAR gene were co-cultured with AS, which is a GD2 positive target tumor cell line, an increase in production of cytokine IFN-γ was observed in γδT cells introduced with GD2-specific CAR. Similarly, when the γδT cells introduced with CD19-specific CAR genes were co-cultured with a CD19 positive tumor cells (NALM6), an increase in production of cytokine IFN-γ was observed in γδT cells introduced with CD19-specific CAR compared to the control.

Example 6

[Recognition of an Antigen-Specific Tumor Cell Line by γδT Cells Introduced with CAR Gene]

Tumor recognition of γδT cells introduced with CAR genes which recognize MAGE-$A4_{p230-239}$ (GVYDGREHTV) in the restriction of HLA-A*02:01 was examined. The results are shown in FIG. 9. When co-culturing (4 hours) with SK-MEL-37 cell line and NW-MEL-38 cell line, which are MAGE-A4 positive HLA-A*02:01 positive cell lines, the expression of CD107a as an index of functional cellular cytotoxicity was confirmed by analysis with flow cytometry. However, low expression of CD107a was shown in the co-culture with Me172 cell lines and HCT116 cell lines, which are MAGE-A4 negative HLA-A*02:01 positive cell lines. As positive control, an HLA-A2 positive T2 cell line (T2-MAGE) added with MAGE-$A4_{p230-239}$ peptide was used. While as negative control, a T2 cell line (T2-ESO1) added with NY-ESO-$1_{p157-165}$ peptide was used.

Example 7

[Tumor-Inhibiting Effect by γδT Cells Introduced with Tumor-Specific TCR and Expressing CD8αβ]

γδT cells were infected with a retroviral vector introduced with TCR (G50 TCR) gene which specifically recognizes NY-ESO-$1_{p157-165}$ peptide in the restriction of HLA-A*02:01, and a retroviral vector which simultaneously expresses a human CD8 α chain and a CD8 β chain. γδT cells expressing CD8αβ, which functions as a sub-stimulation molecule for enhancing the stimulation of TCR (G50 TCR) and TCR were produced. The tumor-inhibiting effect of the cells was examined. For comparison, non-gene modified T cells (NGMC), cells expressing only G50 TCR, and cells expressing only CD8αβ were prepared. These γδT cells were co-cultured with a T2-ESO1 cell line, a T2-MAGE cell line, a NW-MEL-38 cell line and an HCT116 cell line. The production of IFN-γ and CD107a were compared. As a result, the production of IFN-γ and CD107a increased in case of co-culture with T2-ESO1 which is a T2 cell line added with added with NY-ESO-$1_{p157-165}$ peptide, or with NW-MEL-38 which is HLA-A2 positive MAGE-A4 positive cell line. The enhancement was strongly recognized in γδT cells in which G50 TCR was introduced and CD8αβ was expressed compared to that of the γδT cells in which G50 TCR was introduced alone (FIG. 10A).

On Day 0, $4\times10^6$ of tumor cells HCT116 and NW-MEL-38, respectively were transplanted subcutaneously to the left and right back of a NOG mouse to form a tumor. Then, on Day 7, $1\times10^7$ of the four kinds of γδT cells were infused, and the size of the tumor was measured. As a result, in case of co-culture with γδT cells, in mice transplanted with HCT116 cell lines which did not induce the production of IFN-γ and CD107a, no tumor-inhibiting effect was observed even if the γδT cells were infused (FIG. 10B, left figure). However, in mice transplanted with a NW-MEL-38 cell line which induced the production of IFN-γ and CD107a, a remarkable tumor-inhibiting effect was observed in mice infused with γδT cells introduced with G50 TCR and expressing CD8αβ. It is shown that the simultaneous expression of tumor-specific TCR and CD8αβ is effective in tumor inhibition (FIG. 10B, right figure).

Example 8

[Production of a Disease Model Using a NOG Mouse, and Tumor Inhibiting-Effect by γδT Cells Introduced with Tumor-Specific TCR in the Model]

An HLA-A*24:02 positive HTLV-1 positive cell line (TL-Su) introduced with a luciferase gene was produced, and inoculated to a NOG mouse. The tumor formation was visualized by bio-imaging. The γδT cells introduced with tumor-specific TCR were produced according to the method described in Example 2 except that the retroviral vector used was a retroviral vector expressing TCR that specifically recognizes HTLV-1 virus antigen p40Tax-derived peptide (SFHSLHLLF) in the restriction of HLA-A*24:02. NGM-g/d-T cells were used as control cells.

$5\times10^5$ of TL-SU cell lines were implanted subcutaneously in NOG mice (Day 0). After 7 days, $5\times10^6$ of the above genetically modified γδT cells or NGM-g/d-T cells were injected intravenously into the mice (Day 7). Then, after one day (Day 1), 1 week (1 w), 2 weeks (2 w), 3 weeks (3 w), 4 weeks (4 w) and 6 weeks (6 w), the tumor was visualized by bio-imaging. The results are shown in FIG. 11(A). In a mouse in which phosphate buffered saline (PBS) was administered instead of the cells, it was shown that the tumor increased over time. Even when NGM-g/d-T cells were administered, the tumor increased. No tumor-inhibiting effect was observed. However, in the mice administered with the genetically modified γδT cells, almost no increase in tumor was observed. Three weeks later, no tumor was observed. It was shown that the above genetically modified γδT cells exhibit a therapeutic effect of suppressing the increase in tumor and degenerate a tumor in a disease model of NOG mouse. The average radiance in the mice is shown in FIG. 11(B). In the groups of PBS administration and NGM-g/d-T cell administration, the average radiance increased over time. However, in the group of genetically modified γδT cell administration, almost no increase was observed (FIG. 11B).

Example 9

[The Effect of Freezing and Thawing on the Function of the Genetically Modified γδT Cells Stimulated by Compound 7]

To facilitate the treatment of diseases where the transfusion of genetically modified γδT cells is performed, freezing treatment is required in transportation and preservation of the cells. Besides, in order to make the infusion therapy practical, a decrease in cell function due to freezing must be avoided. Thus, cell proliferation was performed in the presence of compound 7 (see Table 1). It was examined whether the function of the γδT cells introduced with foreign genes is affected by freezing.

On Day 0, stimulation culture of monocytes collected by using Ficoll from peripheral blood of healthy human in the presence of compound 7 (1 μM) was started. On Day 1, IL-7 and IL-15 were added to the culture solution to make the final concentration of 25 ng/mL, respectively. On Day 4 and Day 5, NY-ESO-1-specific TCR (G50 TCR) specifically recognizing a complex of HLA-A2 and NY-ESO-$1_{p157\text{-}165}$ peptide (SLLMWITQC) was introduced by using a retroviral vector in the presence of a retronectin. Thereafter, the culture was continued by a culture solution containing IL-7 and IL-15. On Day 12, the cells were frozen, and on Day 13, they were thawed. The cell function was analyzed. For comparison, the function of the cells which were not frozen was analyzed on Day 13 the next day. The results are shown in FIG. 12. As a result of analysis by flow cytometry, there was almost no difference in the expression amount of the introduced NY-ESO-1-specific TCR gene between the frozen and thawed cells (FIG. 12B, upper figure) and the unfrozen cells (FIG. 12A, upper figure). In addition, the genetically modified γδT cells were co-cultured with T2-ESO1 cell line, T2-MAGE cell line, SK-MEL-37 cell line, NW-MEL-38 cell line, MEL72, and HCT116 cell line. The effect of freezing on the genetically modified γδT cells with respect to production of CD107a was analyzed. As a result, there was almost no difference in antigen specificity to the complex of HLA-A2 and NY-ESO-$1_{p157\text{-}165}$ peptide (SLLMWITQC) between frozen and thawed cells (FIG. 12B, lower figure) and unfrozen cells (FIG. 12A, lower figure). It is shown from the results that the function of the genetically modified γδT cells stimulated by compound 7 is not affected by freezing.

Example 10

[Comparison of the Effect of Compound 7 with that of Zoledronate in Terms of Proliferation of γδT Cells and their Purity]

Zoledronate (Zometa) is a compound having the following structure. It is common with compound 7 (see Table 1) in being a nitrogen-containing bisphosphonic acid. Therefore, the usefulness of compound 7 with respect to the zoledronate is examined by using proliferation of the γδT cells and the purity of the γδT cells obtained after the proliferation as index.

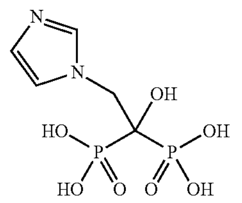 [SMILES: O=P(O)(O)C(O)(Cn1ccnc1)P(=O)(O)O]

Peripheral blood monocytes were collected from healthy subjects (n=8, HD1 to HD8) in two experiments (n=4 in each experiment). On Day 0, $1.5\times10^6$ of the collected peripheral blood monocytes were added to each well of 24-well plate. The stimulation culture was started by yssel's culture solution (1.5 mL) of a variable method containing 10% human AB serum which contained compound 7 (1 μM) or zoledronate (5 μM). Then, on Day 1, IL-2 (300 U/mL) was added. The IL-2 is a cytokine used for the proliferation of the γδT cells according to the reports (non-patent documents 5 and 6). On Day 6, the cells of one well were diluted 2-fold into two wells. The number of cells was counted. On Day 7, the cells of two wells were diluted 2-fold into four wells, and IL-2 (300 U/mL) was further added. On Day 8, half-volume (about 3 mL) of the cells were diluted 6-fold to 18 mL, and cultured in a T75 flask. On Day 8 and Day 11, the number of cells was counted and cell purity was measured by flow cytometry analysis.

With respect to peripheral blood monocytes obtained from each subject, the effect over time of compound 7 (PTA) and zoledronate (Zometa) on cell proliferation is shown in FIG. 13A. On Day 8, almost no difference was confirmed in the effect of compound 7 and zoledronate on cell image proliferation. However, on Day 11, the cell proliferation-stimulating effect of compound 7 (PTA) was strongly recognized in all cells of the subjects HD1 to HD4 of the Experiment 1 compared to that of zoledronate (Zometa). Further, in Experiment 2, the cell proliferation-stimulating effect of compound 7 (PTA) was weak in the cells of subject HD8. However, the effect was the same level in the cells of the subject HDS. In addition, the effect of compound 7 (PTA) was greater than zoledronate (Zometa) in the cells of the subjects HD6 and HD7. The results of Experiment 1 and 2 on Day 11 are summarized in FIG. 13B, and indicated by the average value±standard deviation (n=8). It can be seen that compound 7 (PTA) is significantly excellent in the proliferation of γδT cells compared to zoledronate (Zometa) (p=0.008, t test).

Then, on Day 8 and Day 11, the number of cells was counted and cell purity was measured by flow cytometry analysis. The frequency of the γδT cells in CD3 positive cells (Vd2/CD3) was shown to be significantly higher in the compound 7 (PTA) treatment group compared to the zoledronate (Zometa) treatment group (FIG. 14A). In addition, the frequency of the γδT cells in lymphocyte fraction (P1) (Vd2/P1) in the flow cytometry analysis was also shown to be significantly higher in the compounds 7 (PTA) treatment group on Day 8 and Day 11 compared to the zoledronate (Zometa) treatment group (FIG. 14B). Accordingly, compound 7 (PTA) is shown to be excellent in obtaining highly pure γδT cells as compared with zoledronate (Zometa). T test was used in significant difference assay in FIG. 14.

Test Example

Materials and Methods

1. Preparation of Lymphocytes

Human lymphocytes were obtained by separating peripheral blood mononuclear cells (PBMC) from blood provided by healthy donors using Ficoll-Paque® PLUS (GE Healthcare, catalog number: 17-1440-03). The collection and analysis of a specimen such as human peripheral blood used in this study were performed in accordance with the Helsinki Declaration. Consent of the subjects on documents was achieved in accordance with the protocol approved by the research ethics committee of the medical school of Mie University. The collected specimens were encrypted with no identification of the persons, and stored in a refrigerator and a liquid nitrogen tank in which anti-theft treatment is installed. Personal information on the subjects was anonymized, and severe care and treatment were performed so that individual privacy and gene analysis results did not leak to the outside.

2. Introduction of Gene into Cells

A retroviral vector was used in the introduction of TCR/CAR gene to γδT cells. A multi-dish for floating cells was coated at 500 mL/well at 4° C. for 16 hours or at 25° C. for 2 hours by 20 μg/mL Retronectin® (Takara Bio Inc.) dissolved in a biological preparation reference blood preservation liquid A (ACD-A liquid, TERUMO Corp.). To the multi-dish for floating cells, a virus solution of retroviral vector was added at 1 mL/well, and preloading was performed by centrifugation (2000×g, 2 hours, 32° C.). Subsequently, each well was washed twice with 1 mL of phosphate buffered saline (PBS) containing 1.5% human serum albumin (HSA), and seeded with lymphocytes at $3.8\times10^5$ or less/0.95 mL/well. The cells were precipitated by centrifugation (1000×g, 32° C., 10 minutes). Then, microscopic examination was conducted. It was cultured for one day in an incubator under the environment of 37° C. and 5% $CO_2$ in the presence of a predetermined cytokine (100 IU/mL or 300 IU/mL IL-2, or 25 ng/mL IL-7 and 25 ng/mL IL-15). After 24 hours, the cells were diluted at 4/3-fold, and the gene introduction was performed for the second time in the same manner as that of the first time using the total amount. Afterward, the culture was continued, diluted with 6.8 mL of the culture solution after 4 hours, and cultured again under the environment of 37° C. and 5% $CO_2$. The non-gene modified cells (NGMC) were prepared by applying the same method as the case of preparing gene-introduced cells and culturing for 6 days or more in the presence of the same cytokine.

The introduction experiment of tumor antigen-specific TCR to human peripheral blood monocytes using retrovirus was approved by the examination committee for recombinant DNA experiments of Mie University and research ethics committee of the medical school of Mie University. These experiments were carried out in a laboratory of level P2 which had been approved by the university 3. Flow Cytometry The cells subjected to staining were analyzed by BD FACS Canto® II flow cytometry (Becton Dickinson). γδT cells stimulated in the presence of compound 7 were infected by retrovirus. The cells cultured for 8 to 11 days in which the target TCR or CAR gene was expressed was washed twice with 2% bovine fetal calf serum (FCS)-PBS. Subsequently, 50-fold dilution of a tetramer specific for each TCR/CAR in 2% FCS-PBS was added to the cells and reacted under light-shielding at 37° C. for 15 minutes. Then, the cells were stained at 4° C. and 15 minutes under light shielding by FITC or V500-labeled anti human CD8 antibody (Becton Dickinson) or FITC-labeled anti-human V2δ antibody (Biolegend), washed twice with 2% FCS-PBS, and analyzed by a flow cytometer

4. ELISA

A kit of eBioscience was used for the ELISA. Coating buffer was prepared by diluting 10× coating buffer with distilled water at 10-fold. 48 μL of primary antibody was diluted by mixing with 12 mL of the coating buffer. 100 μL of the diluted solution was added to each well of a 96-well flat bottom plate, and allowed to stand overnight at 4° C. Then, the wells were washed five times with 0.05% PBS-T (a phosphate buffered saline solution containing Tween 20). The assay diluent was prepared by diluting 5× assay diluent with distilled water at 5-fold. 200 μL of the assay diluent was added to each well. Blocking was performed at room temperature for 1 hour. It was then washed five times with 0.05% PBS-T. The standard solutions of IFN-γ were used in which the highest concentration of IFN-γ was set to 1,000 μg/mL, and diluted by 7 stages in the common ratio of 2. The samples and standard solutions were added to each well of the plate, and reacted for 2 hours at room temperature. After the reaction, the wells were washed five times with 0.05% PBS-T. 48 μL of secondary antibody was diluted by mixing with 12 mL the assay diluent. 100 μL of the diluent was added to each well and reacted for 1 hour at room temperature. After the reaction, each well was washed five times with 0.05% PBS-T. 48 μL of horseradish peroxidase was diluted by mixing with 12 mL of the assay diluent. 100 μL of the diluent was added to each well, and reacted at a dark place and room temperature for 30 minutes. Then, each well was washed seven times with 0.05% PBS-T. Then, 100 μL of 3,3',5,5'-tetramethylbenzidine (TMB) substrate solution was added to each well, and reacted for 15 minutes at a dark place and room temperature. 50 μL of 0.18 M sulfuric acid was added to each well to stop the reaction. The absorbance was immediately measured by a microplate reader (Model 680, Bio-Rad) at a wavelength of 450 nm.

5. Intracellular Cytokine Staining

Target cells were prepared at $1\times10^5$ cells/mL, and effector cells were prepared at $1\times10^5$ cells/mL. 0.5 μL of APC anti-human CD107a antibody was added to each sample to make target cells: effector cells=1:1, and co-cultured at 37° C. for 1 hour in a 96-well plate (U bottom). Thereafter, 0.7 μL of Golgistop® (protein transport inhibitor, Becton Dickinson) was added to each well and cultured at 37° C. for 4 hours. The cells of each well were transferred to a V-type 96-well plate, centrifuged at 1200 rpm and 4° C. for 5 minutes, and washed twice with 0.5% BSA/PBS. 0.5 μL of PE-anti-human CD6 antibody was added to each well, allowed to stand light-shielded in ice for 20 minutes, and washed twice with 0.5% BSA/PBS. 100 μL of a cell-fixing solution (Cytofix/Cytoperm®, Becton Dickinson) was added to each well, and allowed to stand in ice for 20 minutes under light-shielding conditions. Then, 100 μL of Perm/Wash® (Becton Dickinson) buffer solution was added to each well and centrifuged. Thereafter, the solution was further washed twice with the Perm/Wash buffer solution. 0.5 μL of V450 IFN-γ or PE-Cy7 TNFα was added to each well. The wells were washed twice with 0.5% BSA/PBS after standing in ice for 30 minutes under light-shielding conditions. Then, measurement was performed by a FACSCanto II flow cytometer (Becton Dickinson), and analysis was performed by using FACS Diva software (Becton Dickinson).

The invention claimed is:

1. A method for producing a γδT cell population expressing a transgene, which comprises Step 1: culturing γδT cells in the presence of tetrakispivaloyloxymethyl 2-(thiazole-2-ylamino) ethylidene-1,1-bisphosphonate or a pharmaceutically acceptable salt thereof;

Step 2: washing the γδT cells cultured in step 1 by centrifugation;

Step 3: culturing the γδT cells washed in step 2 in the presence of IL-7 and IL-15; and Step 4: introducing a gene into the γδT cell cultured in step 3, wherein the gene is NY-ESO-1-specific TCR, HTLV-1 Tax-specific TCR, MAGE-A4-specific TCR, MAGE-A4-specific CAR, CEA-specific CAR, or GD2-specific CAR.

2. The method according to claim 1, wherein the concentration of tetrakispivaloyloxymethyl 2-(thiazole-2-ylamino) ethylidene-1,1-bisphosphonate or a pharmaceutically acceptable salt thereof in step 1 is 0.01 to 1 μM.

3. The method according to claim 1, wherein the γδT cells are derived from a mammal.

4. The method according to claim 3, wherein the mammal is a cancer patient or a non-cancer patient.

5. The method according to claim 4, wherein the cancer is selected from the group consisting of breast cancer, lung cancer, liver cancer, oral cancer, upper pharyngeal carcinoma, head cervical cancer, gastric cancer, esophageal cancer, colon cancer, skin cancer, malignant melanoma, renal cancer, pancreatic cancer, brain tumor, prostate cancer, ovarian cancer, cervical cancer, colorectal cancer, bladder cancer, synovial sarcoma, fat sarcoma, leukemia, malignant lymphoma and multiple myeloma.

6. The method according to claim 1, wherein the step of introducing a gene in step 4 is performed by using a DNA vector or an RNA vector.

7. The method according to claim 1, wherein the step of introducing a gene in step 3 is performed by using a vector selected from the group consisting of a plasmid vector, a lentiviral vector, an adenoviral vector, an adeno-associated virus and a retroviral vector.

8. The method according to claim 1, wherein the step of introducing a gene in step 3 is performed by using a retroviral vector.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: NY-ESO-1p157-165 peptide

<400> SEQUENCE: 1

Ser Leu Leu Met Trp Ile Thr Gln Cys
1 5

<210> SEQ ID NO 2
<211> LENGTH: 9
<212> TYPE: PRT
<213> ORGANISM: Artificial Sequence
<220> FEATURE:
<223> OTHER INFORMATION: HTLV-I virus antigen p40Tax-derived peptide

<400> SEQUENCE: 2

Ser Phe His Ser Leu His Leu Leu Phe
1 5

<210> SEQ ID NO 3
<211> LENGTH: 10
<212> TYPE: PRT
<213> ORGANISM: Artificial Sequence
<220> FEATURE:
<223> OTHER INFORMATION: MAGE-A4p230-239 peptide

<400> SEQUENCE: 3

Gly Val Tyr Asp Gly Arg Glu His Thr Val
1 5 10